(12) United States Patent
Ri

(10) Patent No.: US 9,389,068 B2
(45) Date of Patent: Jul. 12, 2016

(54) METHOD AND DEVICE FOR ANALYSING PHASE DISTRIBUTION OF FRINGE IMAGE USING HIGH-DIMENSIONAL INTENSITY INFORMATION, AND PROGRAM FOR THE SAME

(71) Applicant: NATIONAL INSTITUTE OF ADVANCED INDUSTRIAL SCIENCE AND TECHNOLOGY, Tokyo (JP)

(72) Inventor: Shien Ri, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 22 days.

(21) Appl. No.: 14/383,936

(22) PCT Filed: Dec. 20, 2012

(86) PCT No.: PCT/JP2012/083112
§ 371 (c)(1),
(2) Date: Sep. 9, 2014

(87) PCT Pub. No.: WO2013/136620
PCT Pub. Date: Sep. 19, 2013

(65) Prior Publication Data
US 2015/0049331 A1 Feb. 19, 2015

(30) Foreign Application Priority Data
Mar. 14, 2012 (JP) ................................. 2012-057436

(51) Int. Cl.
*G01B 11/25* (2006.01)
*G01B 11/06* (2006.01)
(Continued)

(52) U.S. Cl.
CPC ............... *G01B 11/25* (2013.01); *G01B 11/06* (2013.01); *G01B 11/2513* (2013.01);
(Continued)

(58) Field of Classification Search
USPC ............... 356/601–614, 73, 237.1, 124–127; 382/154, 168, 186
See application file for complete search history.

(56) References Cited

U.S. PATENT DOCUMENTS

| 5,307,152 | A | * | 4/1994 | Boehnlein | ............. | G06T 7/0057 |
| | | | | | | 250/237 G |
| 6,084,712 | A | * | 7/2000 | Harding | ............... | G01B 11/254 |
| | | | | | | 356/618 |

(Continued)

FOREIGN PATENT DOCUMENTS

| CN | 1554926 A | 12/2004 |
| CN | 101986098 A | 3/2011 |

(Continued)

OTHER PUBLICATIONS

International Search Report mailed Jan. 22, 2013 in corresponding PCT International Application No. PCT/JP2012/083112.

(Continued)

*Primary Examiner* — Sang Nguyen
(74) *Attorney, Agent, or Firm* — Ostrolenk Faber LLP

(57) ABSTRACT

A fringe image phase distribution analysis technique that performs one-dimensional discrete Fourier transform using temporal intensity information or spatial intensity information to calculate the phase distribution of the fringe image. To improve the analysis accuracy of the phase distribution, a plurality of phase-shifted moiré fringe images is generated from high-dimensional intensity data by a thinning-out (down-sampling) process and an image interpolation process, and the phase distribution of the moiré fringe is calculated by a two-dimensional or three-dimensional discrete Fourier transform. In addition, the phase distribution of thinned-out is added to calculate the phase distribution of an original fringe image. Since high-dimensional intensity information which is present in both spatio-domain and temporal-domain is used, phase distribution analysis is less likely to be affected by random noise or vibration. In addition, even when measurement conditions are poor, it is possible to perform phase distribution analysis with high accuracy.

9 Claims, 19 Drawing Sheets

(51) Int. Cl.
*G06T 7/40* (2006.01)
*G01B 11/26* (2006.01)
*G01N 33/483* (2006.01)
*G06T 7/00* (2006.01)
*G01N 21/88* (2006.01)

(52) U.S. Cl.
CPC ........... *G01B 11/26* (2013.01); *G01N 33/4833* (2013.01); *G06T 7/0057* (2013.01); *G06T 7/402* (2013.01); *G01N 2021/8829* (2013.01); *G01N 2021/8887* (2013.01)

(56) References Cited

U.S. PATENT DOCUMENTS

| | | | | |
|---|---|---|---|---|
| 6,392,754 B1 * | 5/2002 | Pingel | ................. | G01B 11/255 356/239.1 |
| 6,788,210 B1 * | 9/2004 | Huang | ................. | G06T 17/10 340/612 |
| 6,816,247 B1 * | 11/2004 | Heppner | ........... | G01M 11/0242 356/124 |
| 2002/0135777 A1 | 9/2002 | Ge | | |

FOREIGN PATENT DOCUMENTS

| | | |
|---|---|---|
| JP | 60-195406 | 10/1985 |
| JP | 2011-174874 | 9/2011 |
| JP | A-2011-226871 A | 11/2011 |
| JP | 4831703 | 12/2011 |

OTHER PUBLICATIONS

J.H. Bruning et al., "Digital Wavefront Measuring Interferometer for Testing Optical Surfaces and Lenses," Applied Optics, vol. 13, No. 11, pp. 2693-2703 (1974).

S. Ri, et al., "Accuracy of the Sampling Moiré Method and Its Application to Deflection Measurements of Large-Scale Structures," Experimental Mechanics; An International Journal, Kluwer Academic Publishers, BO, vol. 52, No. 4, Apr. 7, 2011, pp. 331-340.

S. Ri, et al., "Sampling Moiré Method for Accurate Small Deformation Distribution Measurement," Experimental Mechanics, vol. 50, No. 4, Mar. 13, 2009, pp. 501-508.

Extended European Search Report and European Search Opinion dated in Nov. 24, 2015 in corresponding European Patent Application No. 12871496.1 (8 pages).

* cited by examiner

METHOD AND DEVICE FOR ANALYSING PHASE DISTRIBUTION OF FRINGE IMAGE USING HIGH-DIMENSIONAL INTENSITY INFORMATION, AND PROGRAM FOR THE SAME

CROSS-REFERENCE TO RELATED APPLICATIONS

The present application is a 35 U.S.C. §§371 national phase conversion of PCT/JP2012/083112, filed Dec. 20, 2012, which claims priority to Japanese Patent Application No. 2012-057436, filed Mar. 14, 2012, the contents of both of which are incorporated herein by reference. The PCT International Application was published in the Japanese language.

TECHNICAL FIELD

The present invention relates to a method for analyzing a phase distribution of a fringe image, which can be applied to measurement with higher accuracy than that in the related art by analyzing phase information of a moiré fringe generated from high-dimensional intensity information that is present in spatio- and temporal-domains for single or a plurality of phase-shifted fringe images, and a fringe-image phase distribution analysis device using the same.

BACKGROUND ART

A fringe-image phase analysis technique has been used in many fields. A grating pattern is projected onto the surface of an object to be measured and the phase of a grating image which is distorted depending on the height of the object captured by a camera is analyzed to measure a three-dimensional shape and deformation with high accuracy. A technique is known which measures a very small difference in the optical characteristics, the thickness of a transparent material, refractive index distribution, or an inclination angle of an optical component from the analysis of interference fringes by various types of interferometers using a laser beam obtained by a light interference phenomenon. In addition, a technique is known which analyzes the electromagnetic field from the fringe image obtained by electron beam holography. In the medical field, it is necessary to non-invasively measure the tissue quality (the stereoscopic image of a tissue) of a cell which is a product in tissue engineering. In this case, for example, a phase-shift laser microscope developed by Junji Endo at FK OPT LABO CO., LTD. is used. It is very important to provide an analysis method and an analysis device which can rapidly analyze phase information from one or a plurality of phase-shifted fringe images with high accuracy.

It is necessary to extract the phase information of fringes with high accuracy in order to quantitatively calculate the physical amount (for example, a shape, deformation, distortion, or refractive index) of the object to be measured. For example, a Fourier transform (FFT) method, a wavelet method, or a phase shifting method is used as a method for extracting phase information from a fringe image in the related art. The phase analysis methods are classified into a "temporal phase analysis method" which analyzes the phase of the fringe image using temporal intensity information and a "spatial phase analysis method" which analyzes the phase of the fringe image using spatial intensity information. The spatial analysis method can calculate a phase distribution from one fringe grating image and is suitable for dynamic measurement. In contrast, the temporal analysis method can calculate a phase for each pixel of the camera and is suitable for high-resolution analysis.

A phase shifting method has been proposed as one temporal analysis method (Non-patent Document 1). The phase shifting method calculates a phase distribution from T-step digital image data items (hereinafter, a captured digital image with a grating pattern is referred to as a "fringe image") with an intensity distribution I (x, y; t) represented by the following expression.

Expression 1

$$I(x, y; t) = I_a(x, y)\cos\left\{2\pi\frac{x}{P} + \varphi_0(x, y) + 2\pi\frac{t}{T}\right\} + I_b(x, y) \quad (1)$$

$$= I_a(x, y)\cos\left\{\varphi(x, y) + 2\pi\frac{t}{T}\right\} + I_b(x, y), \quad (t = 0 \sim T-1)$$

Here, $I_a$ and $I_b$ indicate the intensity of amplitude (an amplitude component with a frequency 1) and the intensity of a background (an amplitude component with a frequency 0) of the fringe grating, respectively. In addition, P indicates the pitch of the fringe grating, $\varphi_0$ indicates the initial phase of the fringe grating, and $\varphi$ indicates the phase value of the fringe image to be finally calculated. Furthermore, x and y indicate position coordinates (in general, integers) on an optical digital camera (the term "optical digital camera" means a digital camera or a video camera which can capture digital image data, regardless of the type of imaging element, such as a CCD sensor or a CMOS sensor and is hereinafter referred to as a "camera"). In addition, t indicates the serial numbers of a plurality of grating images and $2\pi t/T$ is a term indicating a phase-shift. In Expression (1), discrete Fourier transform (DFT) is applied to "t" to calculate the angle of deviation of the component with the frequency 1. In this way, the phase distribution is obtained.

Expression 2

$$\varphi(x, y) = -\arctan\frac{\sum_{t=0}^{T-1} I(x, y; t)\sin(2\pi t/T)}{\sum_{t=0}^{T-1} I(x, y; t)\cos(2\pi t/T)} \quad (2)$$

A grating projection method or a method for measuring the phase of a fringe image using an interferometer generates T-step phase-shifted fringe grating patterns, captures the T-step phase-shifted fringe grating patterns using an optical camera to obtain a plurality of fringe grating images, and analyzes the plurality of fringe grating images using Expression (2). The intensity of the amplitude $I_a$ and the intensity of the background $I_b$ of the fringe grating can be calculated by Expression (3) and Expression (4).

Expression 3

$$I_a(x, y) = \frac{2}{N}\sqrt{\left[\sum_{t=0}^{T-1} I(x, y; t)\cos\frac{2\pi t}{T}\right]^2 + \left[\sum_{t=0}^{T-1} I(x, y; t)\sin\frac{2\pi t}{T}\right]^2} \quad (3)$$

Expression 4

$$I_b(x, y) = \frac{1}{N}\left[\sum_{t=0}^{T-1} I(x, y; t)\right] \quad (4)$$

In contrast, in the spatial analysis method according to the related art, a sampling moiré method has been proposed (Patent Document 1). The sampling moiré method calculates a phase distribution from a plurality of phase-shifted moiré fringes which are obtained by down-sampling (thinning out) one fringe grating image at an interval close to the pitch of the original grating. FIG. 1 shows the thinning-out process and the intensity interpolation process which are used in the sampling moiré method disclosed in Patent Document 1. Here, the "thinning-out process" extracts intensity data for every M pixel which is arranged at a predetermined interval from the left end or the right end of one fringe grating image (FIG. 1(a)) recorded on the camera. As shown in FIG. 1(b), a plurality of starting points of thinning-out can be changed to obtain a plurality of thinned-off images from one image. In addition, the "intensity interpolation" process interpolates some omitted intensity data using peripheral intensity data, as shown in FIG. 1(c).

FIG. 2 shows the principle of one-shot fringe grating image phase analysis by a one-dimensional sampling moiré method according to the related art. When an optical camera captures the image of an object with a regular grating pattern (FIG. 2(a)), one fringe grating image is obtained. In particular, when a change in the intensity of the grating pattern is a sine wave or a cosine wave, it is represented by Expression (5).

Expression 5

$$I(x, y) = I_a \cos\left\{2\pi \frac{x}{P} + \varphi_0(x, y)\right\} + I_b = I_a \cos\{\varphi(x, y)\} + I_b \quad (5)$$

Here, x and y indicate position coordinates (in general, integers) on the camera and $I_a$ and $I_b$ indicate the intensity of amplitude (an amplitude component with a frequency 1) and the intensity of a background (an amplitude component with a frequency 0) of a fringe grating, respectively. In addition, $\phi 0$ indicates the initial phase of the fringe grating and $\phi$ indicates the phase value of the fringe image to be finally calculated. Furthermore, P indicates a pitch on the captured image. When an image thinning-out process is performed on the captured one fringe grating image at a pitch M (M is generally an integer) close to P and intensity interpolation is performed using the intensity values of adjacent images, it is possible to obtain a fringe image (hereinafter, referred to as a "moiré fringe image") with a low spatial frequency, that is, a large pitch. In addition, when the intensity interpolation is performed while changing a starting point m of thinning-out one pixel-by-one pixel, M-step phase-shifted moiré fringe images are obtained, as shown in FIG. 2(b), and can be represented by Expression (6).

Expression 6

$$I_{moire}(x, y; m) = I_a \cos\left\{2\pi\left(\frac{1}{P} - \frac{1}{M}\right)x + \varphi_0(x, y) + 2\pi\frac{m}{M}\right\} + I_b \quad (6)$$
$$= I_o \cos\left\{\varphi_{moire}(x, y) + 2\pi\frac{m}{M}\right\} + I_b$$

The phase of the moiré fringe is shifted from the starting point m of thinning-out by $2\pi/M$. When one-dimensional discrete Fourier transform (DFT) is applied to "m" in Expression (6), it is possible to calculate the phase distribution $\phi_{moire}(x, y)$ of the moiré fringe, as shown in FIG. 2(c).

Expression 7

$$\varphi_{moire}(x, y) = -\arctan\frac{\sum_{t=0}^{T-1} I_{moire}(x, y; m)\sin(2\pi m/M)}{\sum_{t=0}^{T-1} I_{moire}(x, y; m)\cos(2\pi m/M)} \quad (7)$$

As shown in Expression (8), the phase distribution of the fringe grating (FIG. 2(d)) can be calculated by adding the phase distribution of the sampling point in the thinning-out process to the phase distribution of the moiré fringe.

Expression 8

$$\varphi(x, y) = \varphi_{moire}(x, y) + 2\pi\frac{x}{M} \quad (8)$$

Expression (8) makes it possible to calculate the phase distribution of the fringe grating using one fringe grating image.

In any method according to the related art, the phase is calculated by one-dimensional discrete Fourier transform, only using one-dimensional phase-shifted intensity information, such as space or time.

PRIOR ART DOCUMENTS

Patent Documents

[Patent Document 1] Japanese Patent No. 4831703, Title of the Invention: Method for Measuring Displacement of Object, Inventors: Motoharu FUJIGAKI, Shien RI, and Yoshiharu MORIMOTO, Applicant: Wakayama University Non-Patent Documents

[Non-Patent Document 1] Bruning, J. H. et al, Digital Wavefront Measuring Interferometer for Testing Optical Surfaces and Lenses, Applied Optics, Vol. 13, No. 11, pp. 2693-2703 (1974).

DISCLOSURE OF INVENTION

Problems to be Solved by the Invention

In the phase analysis technique according to the related art, one-dimensional discrete Fourier transform is performed on temporal intensity information or spatial intensity information to calculate the phase. However, the relationship between a variation $\sigma_{\phi n}$ in the phase error and the number of phase-shifts N has been expressed using Expression (9).

Expression 9

$$\sigma_{\phi n} = \frac{\sigma_n}{I_a}\sqrt{\frac{2}{N}} = \frac{1}{SNR} \cdot \frac{\sqrt{2}}{\sqrt{N}} \quad (9)$$

Here, $\sigma_n$ is a standard deviation of random noise and $SNR = I_a/\sigma_n$ is a signal-to-noise ratio. The variation in the phase error is inversely proportional to the square root of the number of captured images N and the SNR of the captured image and is $2^{1/2}$ times the product of the two parameters. Therefore, when the number of phase-shifts increases to acquire a large number of grating images, the accuracy of phase analysis is expected to be improved. For example, it is necessary to increase the number of phase-shifted images 100 times in order to improve the measurement accuracy 10 times. However, there is a dilemma that, since the number of captured images increases exponentially, the measurement speed is significantly reduced.

In measurement in various fields, in some cases, the contrast (SNR) of the acquired fringe image is reduced due to very large or very small reflectance of the object to be measured, which results in a large error in the analysis result of the phase, or a large measurement error occurs when an error is included in the amount of phase-shift due to an environmental vibration during measurement or the performance of the phase-shift device. There is a demand for a technique which can further improve the analysis accuracy of the phase, without increasing the measurement time.

Means for Solving the Problems

The present invention has been made in view of the above-mentioned circumstances and provides a technique which performs phase analysis with higher accuracy than a method according to the related art even in a fringe grating image which has low SNR or includes a phase-shift error, without increasing the number of captured images.

As the first aspect, the present invention provides a method for analyzing a phase distribution of a fringe image that calculates a phase distribution of a fringe image obtained by capturing a fringe pattern on a surface of an object using an optical digital camera including an imaging element arranged in a horizontal direction and a vertical direction. The method includes: a step of obtaining one two-dimensional fringe image or a three-dimensional fringe image in which a plurality of two-dimensional fringe images are arranged in time series by capturing one image of the fringe pattern on the surface of the object or a plurality of images of the fringe pattern while shifting a temporal phase; a step of generating a plurality of phase-shifted moiré fringe images by performing at least a thinning-out process on intensity data of the one two-dimensional fringe image or the three-dimensional fringe image; a step of calculating a phase distribution of the moiré fringe images in the horizontal direction or the vertical direction by using fast Fourier transform or discrete Fourier transform on the phase-shifted moiré fringe images; and a step of calculating the phase distribution of the fringe pattern image on the object by adding a phase value of a thinning-out point in the thinning-out process to a value of each point in the phase distribution.

In addition, in the present invention, the step of obtaining the two-dimensional fringe image includes capturing the fringe pattern that is arranged on the surface of the object so as to be inclined in one direction or two directions perpendicular to each other with respect to the arrangement of the imaging element of the optical digital camera in the horizontal and vertical directions. The step of generating the plurality of phase-shifted moiré fringe images may include: a sub-step of performing M thinning-out processes and N thinning-out processes (M and N are an integer equal to or greater than 3) on the two-dimensional fringe image while sequentially changing starting pixels in the horizontal direction and the vertical direction for every M pixels and every N pixels which are arranged at equal intervals in the horizontal direction and the vertical direction, respectively; and a sub-step of generating M×N-step moiré fringe images by performing an intensity value interpolation process on each of the images thinned out in the horizontal or vertical direction which are obtained by the thinning-out processes.

The method for analyzing a phase distribution of a fringe image is a method which analyzes a spatial phase using one two-dimensional fringe image obtained by capturing an inclined fringe pattern.

In addition, in the present invention, the step of obtaining the three-dimensional fringe image includes obtaining a plurality of phase-shifted two-dimensional fringe images by capturing T-step images (T is an integer equal to or greater than 3) of the fringe pattern that is arranged on the surface of the object in the horizontal direction or the vertical direction or is arranged in a grating shape in the horizontal direction and the vertical direction, with respect to the arrangement of the imaging element of the optical digital camera in the horizontal and vertical directions, while shifting the temporal phase. The step of generating the plurality of phase-shifted moiré fringe images may include: a pre-processing sub-step of converting the T-step two-dimensional fringe images whose temporal phases are shifted into T-step normalized two-dimensional fringe images with a constant intensity of amplitude, using an intensity of amplitude and an intensity distribution of a background calculated by a phase shifting method, when the intensity distribution of amplitude of the lattice-shaped fringe pattern is not constant; a thinning-out sub-step of sampling every M pixels which are arranged at equal intervals in the horizontal direction or the vertical direction in each of the T-step two-dimensional fringe images with a constant intensity of amplitude whose temporal phases are shifted; and a sub-step of generating M×T-step moiré fringe images by performing an intensity value interpolation process on each of the M-step images which are thinned-out in the horizontal direction or the vertical direction by the thinning-out process.

The method for analyzing a phase distribution of a fringe image is a basic method of spatiotemporal phase analysis using a three-dimensional fringe image (a plurality of two-dimensional fringe images) obtained by shifting a temporal phase, arranging a parallel fringe pattern or a lattice-shaped fringe pattern in the horizontal (or vertical) direction of the imaging element of the camera, and capturing the pattern.

In addition, in the present invention, the step of obtaining the three-dimensional fringe image comprises obtaining a plurality of phase-shifted two-dimensional fringe images by capturing T-step images (T is an integer equal to or greater than 3) of the fringe pattern that is arranged on the surface of the object so as to be inclined in one direction or to be inclined in a lattice shape in two directions perpendicular to each other with respect to the arrangement of the imaging element of the optical digital camera in the horizontal and vertical directions, while shifting the temporal phase. The step of generating the plurality of phase-shifted moiré fringe images may include: a pre-processing sub-step of converting the T-step two-dimensional fringe images whose temporal phases are shifted into T-step normalized two-dimensional fringe images with a constant intensity of amplitude, using an intensity of amplitude and an intensity distribution of a background calculated by a phase shifting method, only when the intensity distribution of the amplitude of the fringe pattern is not constant; a sub-step of performing M thinning-out processes and N thinning-out processes on each of the two-dimensional fringe images with the constant intensity of the amplitude while sequentially changing starting pixels in the horizontal direction and the vertical direction for every M pixels and every N pixels which are arranged at equal intervals in the horizontal direction and the vertical direction, respectively; and a sub-step of generating M×N×T-step moiré fringe images for the T-step two-dimensional fringe images whose temporal phases are shifted by using the sub-step of performing the intensity value interpolation process on each of the images which are thinned out in the horizontal direction or the vertical direction by the thinning-out process to generate M×T-step moiré fringe images.

The method for analyzing a phase distribution of a fringe image is a high-accuracy spatiotemporal phase analysis method using a three-dimensional fringe image (a plurality of two-dimensional fringe images) obtained by shifting a temporal phase, inclining a parallel fringe pattern or a lattice-shaped fringe pattern in the horizontal (or vertical) direction of the imaging element of the camera, and capturing the pattern.

Furthermore, the present invention provides a measurement device which measures a three-dimensional shape, displacement, and distortion distribution of a structure and performs any one of the above-mentioned methods for analyzing a phase distribution of a fringe image.

The present invention provides a measurement device which measures a thickness, refractive index distribution, or inclination angle of an optical component and a transparent object and performs any one of the above-mentioned methods for analyzing a phase distribution of a fringe image.

The present invention provides a measurement device which detects a defect of an object using phase information of an ultrasonic image, detects anomalous displacement to detect a landslide, evaluates integrity of an infrastructure, and performs any one of the above-mentioned methods for analyzing a phase distribution of a fringe image.

The present invention provides a measurement device which non-invasively analyzes and evaluates a cell tissue of a living body and performs any one of the above-mentioned methods for analyzing a phase distribution of a fringe image.

Finally, the present invention provides a program for analyzing a phase distribution of a fringe image which executes any one of methods for analyzing a phase distribution of a fringe image described above.

Effects of the Invention

According to the present invention, it is possible to analyze the phase information of a fringe image with high accuracy, using the same number of captured images as that in the method according to the related art.

As the first effect, it is possible to achieve the same accuracy as that in the related art even when an inexpensive imaging element (cost down) is used.

As the second effect, it is possible to perform analysis even under very bright or dark conditions and to extend a measurement range.

As the third effect, it is possible to reduce the influence of vibration and the present invention can be applied to measure in the field.

However, in the present invention, since local spatial intensity information is used, it is noted that spatial resolution is a little lower than that in the method according to the related art.

The present invention has the following advantages.

As advantage 1, in the case of ultrafast measurement, since the exposure time is short, the S/N ratio is reduced and it is possible to reduce a measurement error.

As advantage 2, it is possible to perform measurement in an environment in which a large amount of vibration occurs (measurement in the field, not on a vibration isolator in a laboratory).

As advantage 3, it is possible to analyze a phase even when an object has very low reflectance and the contrast of a fringe image is very low.

EMBODIMENTS FOR CARRYING OUT THE INVENTION

EXAMPLE 1

Figure 1:
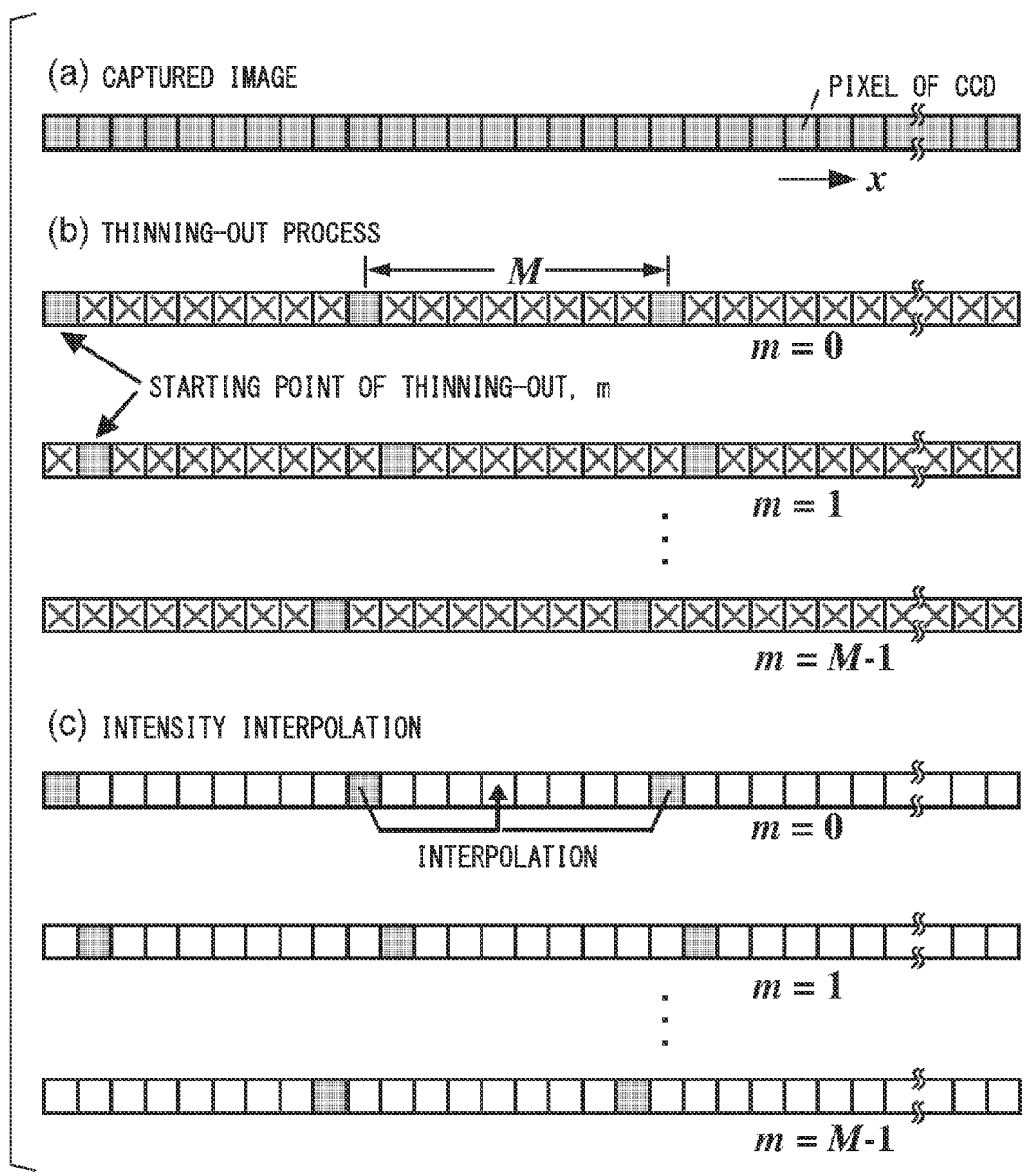
FIG. 1 is a diagram illustrating an image processing method in a one-dimensional sampling moiré method.
Figure 2:
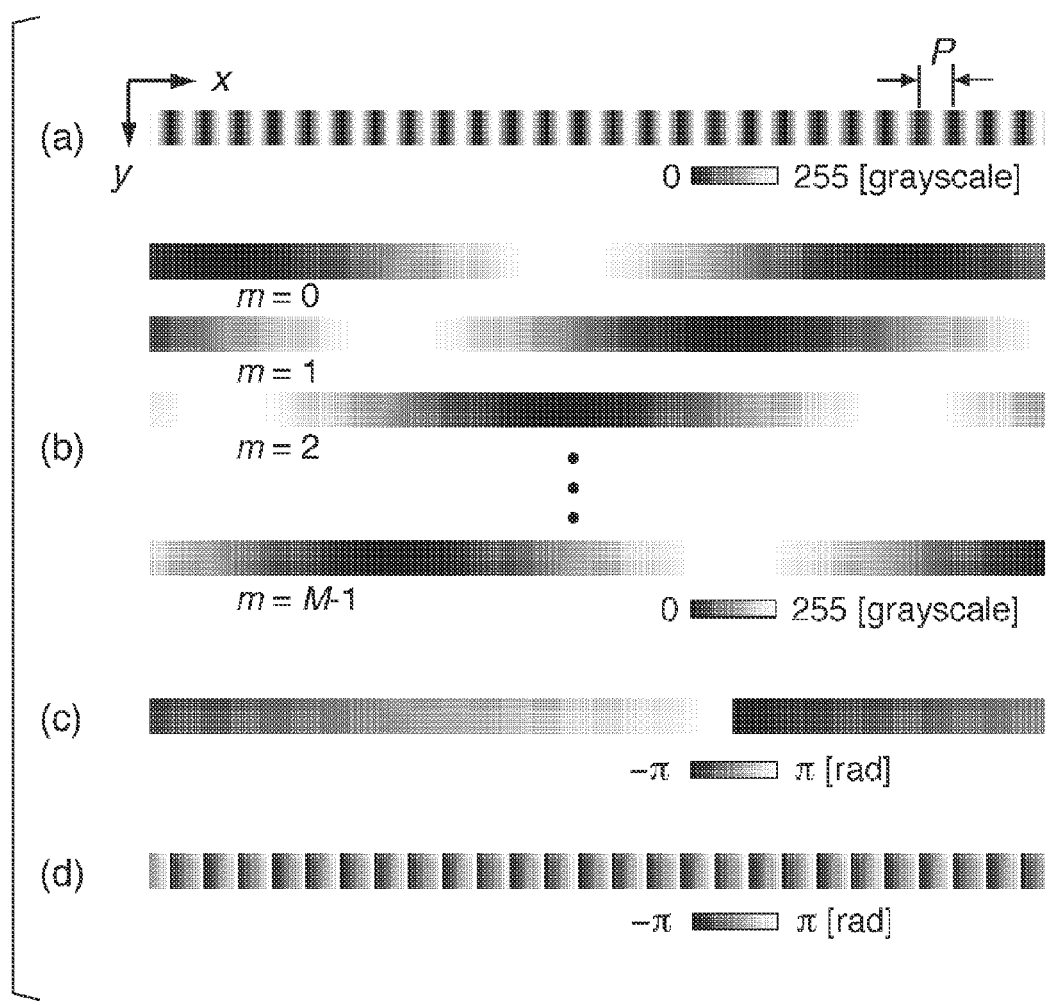
FIG. 2 is a diagram illustrating the principle of one-shot fringe grating image phase analysis by the one-dimensional sampling moiré method.
Figure 3:
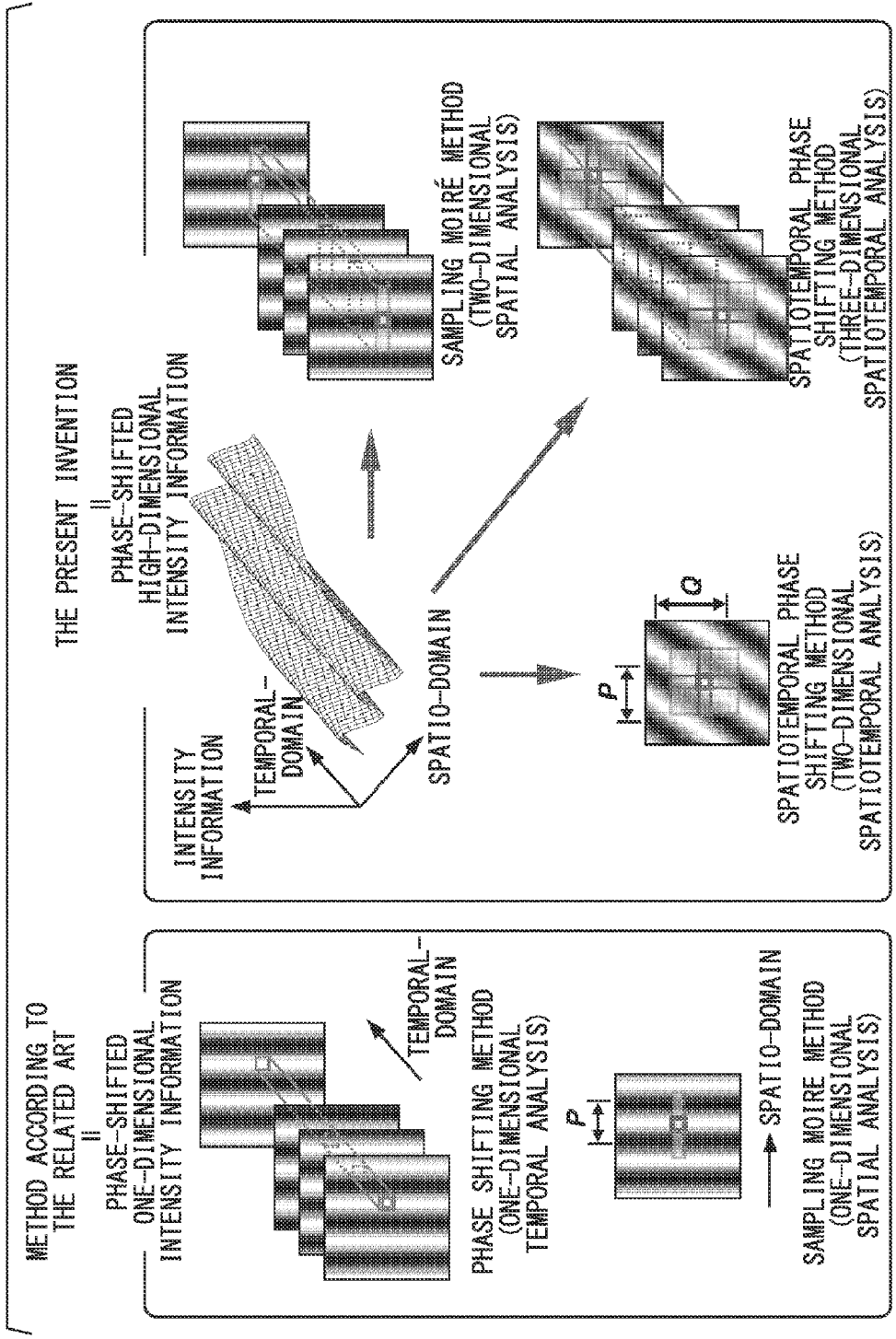
FIG. 3 is a diagram illustrating the relationship between a phase analysis method using one-dimensional intensity information according to the related art and a phase analysis method using high-dimensional intensity information according to the present invention.

A phase analysis method based on the present invention is shown in FIG. 3. The phase shifting method according to the related art uses only one-dimensional intensity information, such as a change in intensity on the temporal-domain, and the sampling moiré method according to the related art uses only one-dimensional intensity information, such as a change in intensity on the spatio-domain. In contrast, in the present invention, a plurality of phase-shifted moiré fringe images is generated from high-dimensional intensity data by a thinning-out process and an image interpolation process and a phase distribution of a moiré fringe is calculated by two-dimensional or three-dimensional discrete Fourier transform. In addition, there is a method which adds a thinned phase distribution to calculate the phase distribution of the original fringe image. Since high-dimensional intensity information which is present in space and time is used, it is less likely to be affected by random noise or vibration than one-dimensional intensity information according to the related art. Therefore, even when measurement conditions are bad, it is possible to perform phase analysis with high accuracy.

In the present invention, three processing methods shown on the right side of FIG. 3 will be described, according to the number of acquired fringe images and the shape of a lattice. Each of the process methods will be described in detail below.

Table 1 shows some methods for acquiring fringe images in the present invention, but the method for acquiring the fringe images is not limited thereto.

term "inclination" means that the fringe grating is inclined in the coordinate system of a camera in which an imaging element is arranged in the horizontal direction and the vertical direction. It is preferable that the fringe grating on the surface of the object to be measured be inclined. However, the fringe grating may not be inclined) is projected onto or attached to the surface of the object to be measured and is captured by an optical camera, single fringe grating image having an intensity distribution represented by Expression (10) is obtained:

Expression 10

$$I(x, y) = I_a \cos\left\{2\pi \frac{x}{P} + 2\pi \frac{y}{Q} + \varphi_0(x, y)\right\} + I_b = I_a \cos\{\varphi(x, y)\} + I_b \quad (10)$$

Here, P and Q indicate a grating pitch in the x direction or the y direction on a captured image.

A thinning-out process is performed on the captured one fringe grating image while changing a starting point m of thinning-out one pixel-by-one pixel in the x direction at a pitch M (in general, an integer) which is close to P for each pixel and a process 41 which performs intensity interpolation using the intensity values of adjacent images is performed to obtain M-step phase-shifted moiré fringe images. Then, the thinning-out process is further performed on the M-step moiré fringe images obtained by the thinning-out process and the intensity interpolation while changing a starting point n of thinning-out one pixel-by-one pixel in the y direction and a process 42 which performs intensity interpolation using the intensity values of adjacent images is performed to obtain M×N-step phase-shifted moiré fringe images. The M×N-step moiré fringe images can be represented by Expression (11). The thinning-out order is the same when the thinning-out

TABLE 1

| | Method for generating fringe image | | | Phase shifting method | Method for acquiring inclined fringe image | | |
|---|---|---|---|---|---|---|---|
| | | | | | Hardware manner | | Software |
| Type | Method | Form | Object | | Grating side | Camera side | manner |
| Attachment | Grating is printed and used | Contact | General purpose | X | Obliquely attached | Camera is inclined at 45° and captures images | Fringe image is rotated at 45° on software |
| Projection | Projector is used | Non-contact | Diffuser | Phase-shifted image is prepared | Inclined grating is prepared | | |
| Display | Liquid crystal monitor is used | Non-contact | Mirror-surface object | Phase-shifted image is prepared | Inclined grating is prepared | | |
| Interference | Laser beam is used | Non-contact | General purpose | 1) Reference mirror is moved | Slightly inclined | | |
| | | | | 2) Wedge prism is inserted | X | | |
| | | | | 3) Wavelength-variable laser is used | X | | |
| | | | | 4) Wave plate is rotated | X | | |

In the present invention, first, a two-dimensional sampling moiré method (two-dimensional spatial analysis method), which is a first method, will be described.

Figure 4:
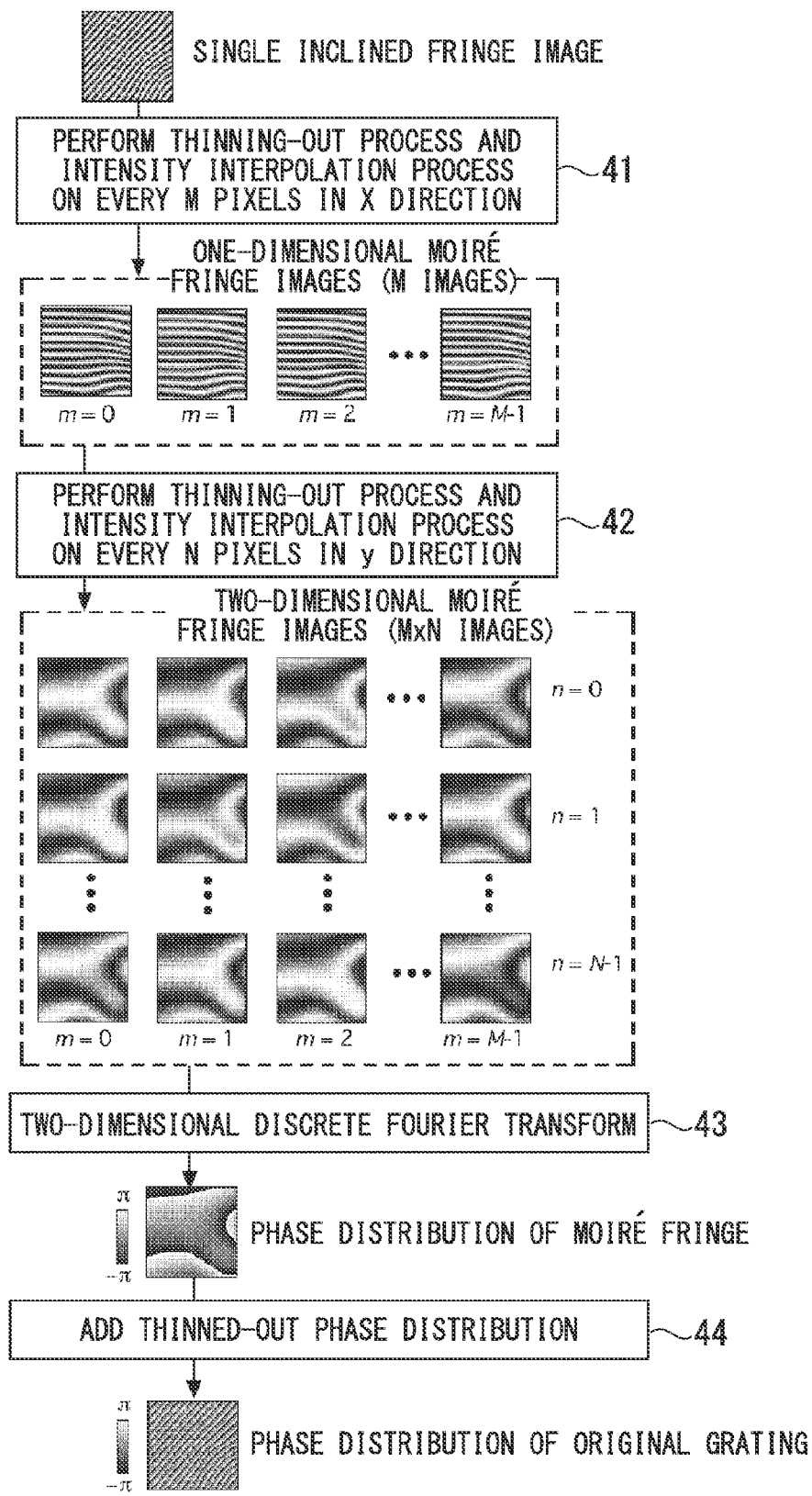
FIG. 4 is a diagram illustrating the principle of one-shot fringe grating image phase analysis by a two-dimensional sampling moiré method and the outline of the flow of an image processing method.

FIG. 4 shows the principle of one-shot fringe grating image phase analysis by the two-dimensional sampling moiré method and the flow of an image processing method. When single inclined fringe grating (in the present invention, the process and the intensity interpolation process in the x direction are performed and then the thinning-out process and the intensity interpolation process in the y direction are performed and when the thinning-out process and the intensity interpolation process in the y direction are performed and then the thinning-out process and the intensity interpolation process in the x direction are performed.

Expression 11

$$I_{moire}(x, y; m, n) = \qquad(11)$$
$$I_a\cos\left\{2\pi\left(\frac{1}{P} - \frac{1}{M}\right)x + 2\pi\left(\frac{1}{Q} - \frac{1}{N}\right)y + \varphi_0(x, y) + 2\pi\frac{m}{M} + 2\pi\frac{n}{N}\right\} +$$
$$I_b = I_a\cos\left\{\varphi_{moire}(x, y) + 2\pi\frac{m}{M} + 2\pi\frac{n}{N}\right\} + I_b$$

The phase of the moiré fringe obtained by the thinning-out process and the intensity interpolation process is shifted by $2\pi/M$ or $2\pi/N$ from the starting points m of thinning-out and n in the x direction or the y direction. Therefore, when two-dimensional discrete Fourier transform, which is a process 43, is applied to m and n in Expression (11), the phase distribution $\varphi_{moire}(x, y)$ of the moiré fringe can be calculated by Expression (12).

Expression 12

$$\varphi_{moire}(x, y) = -\arctan\frac{\sum_{m=0}^{M-1}\sum_{n=0}^{N-1}I_{moire}(x, y; m, n)\sin(2\pi m/M + 2\pi n/N)}{\sum_{m=0}^{M-1}\sum_{n=0}^{N-1}I_{moire}(x, y; m, n)\cos(2\pi m/M + 2\pi n/N)} \qquad(12)$$

As shown in Expression (13), the phase distribution of the original grating can be calculated by adding the phase distribution of a sampling point in the thinning-out process performed in the x direction and the y direction, which is a process 44, to the phase distribution of the moiré fringe.

Expression 13

$$\varphi(x, y) = \varphi_{moire}(x, y) + 2\pi\frac{x}{M} + 2\pi\frac{y}{N} \qquad(13)$$

EXAMPLE 2

Next, in the present invention, a spatiotemporal phase shifting method (two-dimensional spatiotemporal analysis), which is a second method, will be described.

Figure 5:
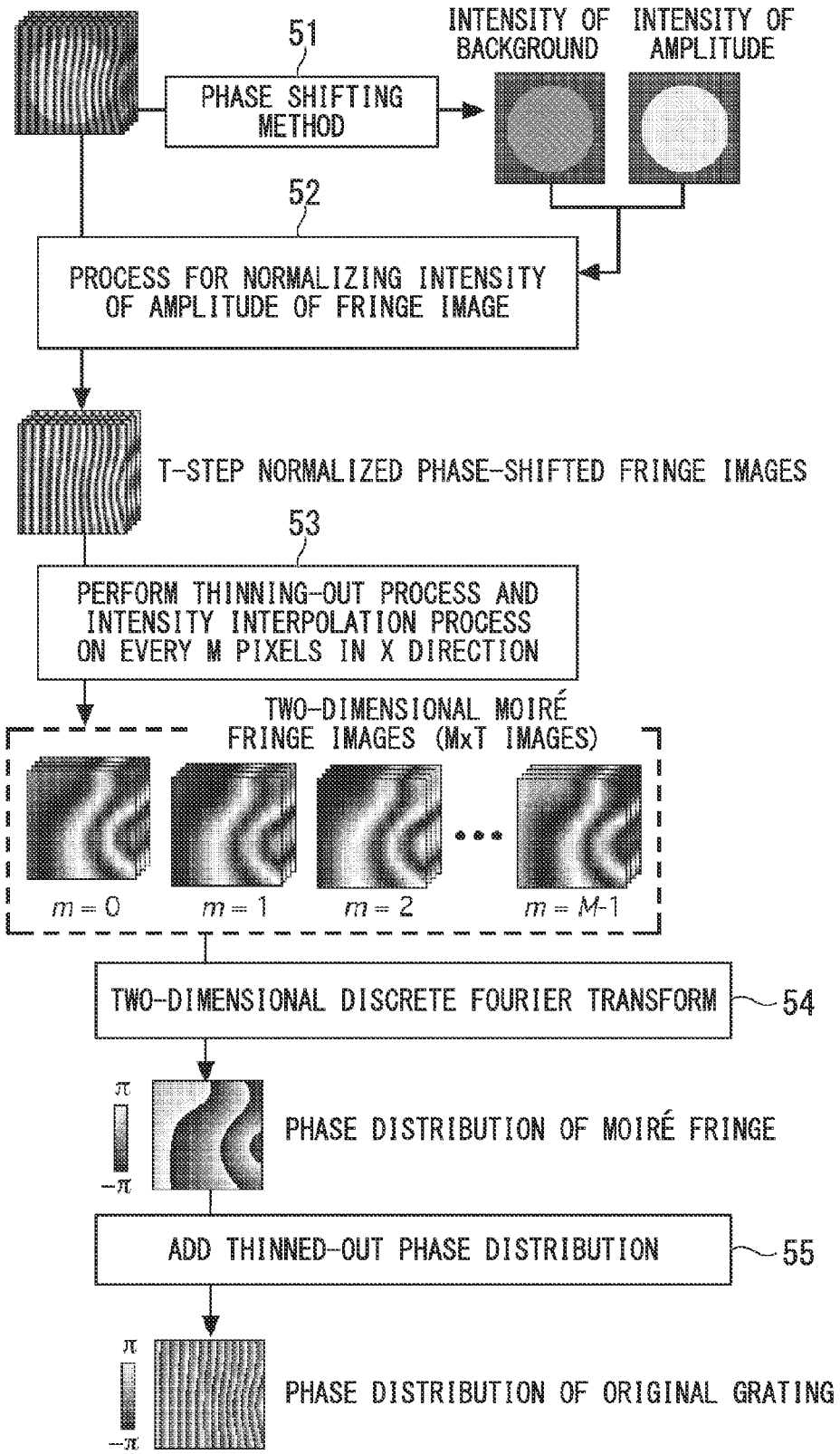
FIG. 5 is a diagram illustrating the principle of fringe grating image phase analysis by a two-dimensional spatiotemporal phase shifting method and the outline of the flow of an image processing method.

FIG. 5 shows the principle of the phase analysis of a fringe grating image by the two-dimensional spatiotemporal phase shifting method and the flow of an image processing method. When an optical camera is used to capture T-step phase-shifted fringe grating images using the same method as that in the related art, the intensity distribution represented by Expression (1) is obtained. Here, an intensity of amplitude varies depending on, for example, a material forming the object to be measured and the reflectance and surface shape of the object to be measured. First, an intensity of amplitude normalization process is performed as pre-processing. First, the intensity of amplitude $I_a$ and the intensity of a background $I_b$ of the fringe grating are calculated by a calculation method as a phase shifting method, which is a process 51 according to the related art, using Expression (3) and Expression (4). Then, the T-step phase-shifted fringe gratings are converted into normalized fringe grating images having an intensity of amplitude of 1 and an intensity of a background of 0 by a process 52 represented by Expression (14). In addition, when the captured fringe image has a constant intensity of amplitude, the normalization process for the captured fringe image can be omitted.

Expression 14

$$\bar{I}(x, y; t) = \frac{I(x, y; t) - I_b(x, y)}{I_a(x, y)} \qquad(14)$$
$$= \cos\left\{2\pi\frac{x}{P} + \varphi_0(x, y) + 2\pi\frac{t}{T}\right\}$$
$$= \cos\left\{\varphi(x, y) + 2\pi\frac{t}{T}\right\}, (t = 0 \sim T - 1)$$

A process 53 which performs down sampling (thinning-out process) and intensity interpolation in the x direction or the y direction is performed on the T-step normalized fringe images to obtain M×T-step phase-shifted moiré fringe images represented by Expression (15).

Expression 15

$$\bar{I}_{moire}(x, y; m, t) = \cos\left\{2\pi\left(\frac{1}{P} - \frac{1}{M}\right)x + \varphi_0(x, y) + 2\pi\frac{m}{M} + 2\pi\frac{t}{T}\right\} \qquad(15)$$
$$= \cos\left\{\varphi_{moire}(x, y) + 2\pi\frac{m}{M} + 2\pi\frac{t}{T}\right\}$$

In Expression (15), $2\pi m/M$ means a spatial phase-shift and $2\pi t/T$ means a temporal phase-shift. Two-dimensional discrete Fourier transform, which is a process 54 related to variables m and t in Expression (15), is applied to calculate the angle of deviation of a component with a frequency 1. In this way, the phase distribution of the moiré fringe represented by the following expression is obtained.

Expression 16

$$\bar{\varphi}_{moire}(x, y) = -\arctan\frac{\sum_{m=0}^{M-1}\sum_{t=0}^{T-1}\bar{I}_{moire}(x, y; m, t)\sin(2\pi m/M + 2\pi t/T)}{\sum_{m=0}^{M-1}\sum_{t=0}^{T-1}\bar{I}_{moire}(x, y; m, t)\cos(2\pi m/M + 2\pi t/T)} \qquad(16)$$

As shown in Expression (19), the phase distribution of the original grating represented by the following Expression (17) can be calculated by adding the phase distribution of a sampling point in a thinning-out process, which is a process 55, to the phase distribution of the moiré fringe represented by the following Expression (18).

Expression 17

$$\bar{\varphi}(x,y) \qquad(17)$$

Expression 18

$$\bar{\varphi}_{moire}(x,y) \qquad(18)$$

Expression 19

$$\bar{\varphi}(x, y) = \bar{\varphi}_{moire}(x, y) + 2\pi\frac{x}{M} \qquad(19)$$

EXAMPLE 3

Finally, a spatiotemporal phase shifting method (three-dimensional spatiotemporal analysis) will be described as a third method.

Figure 6:
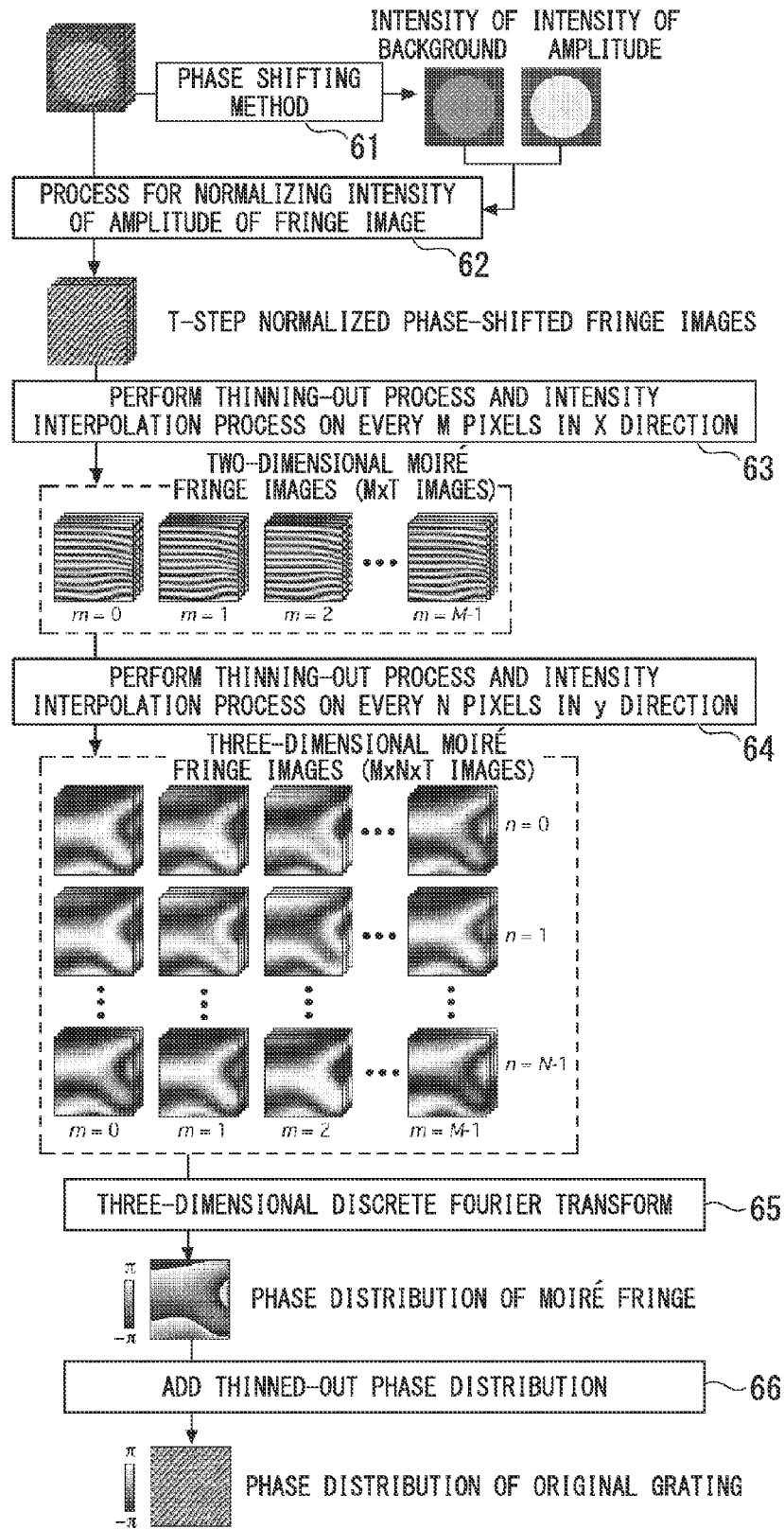
FIG. 6 is a diagram illustrating the principle of fringe grating image phase analysis by a three-dimensional spatiotemporal phase shifting method and the outline of the flow of an image processing method.

FIG. 6 shows the principle of the phase analysis of a fringe grating image by a three-dimensional spatiotemporal phase shifting method and the flow of an image processing method. When an optical camera is used to capture T-step phase-shifted inclined fringe grating images, an intensity distribution represented by Expression (20) is obtained.

Expression 20

$$I(x, y; t) = I_a(x, y)\cos\left\{2\pi\frac{x}{P} + 2\pi\frac{y}{Q} + \varphi_0(x, y) + 2\pi\frac{t}{T}\right\} + \\ I_b(x, y) \\ = I_a(x, y)\cos\left\{\varphi(x, y) + 2\pi\frac{t}{T}\right\} + I_b(x, y), (t = 0 \sim T - 1)$$ (20)

Similarly to the second method, an intensity of amplitude varies depending on, for example, a material forming the object to be measured and the reflectance and surface shape of the object to be measured. For this reason, the T-step phase-shifted inclined fringe grating images are converted into normalized fringe grating images having an intensity of amplitude of 1 and an intensity of a background of 0 by preprocessing for normalizing the intensity of amplitude in a process 61 and a process 62. In addition, when the captured fringe image has a constant intensity of amplitude, the normalization process for the captured fringe image can be omitted.

Expression 21

$$\bar{I}(x, y; t) = \frac{I(x, y; t) - I_b(x, y)}{I_a(x, y)} \\ = \cos\left\{2\pi\frac{x}{P} + 2\pi\frac{y}{Q} + \varphi_0(x, y) + 2\pi\frac{t}{T}\right\} \\ = \cos\left\{\varphi(x, y) + 2\pi\frac{t}{T}\right\}, (t = 0 \sim T - 1)$$ (21)

Processes 63 and 64 which perform a down sampling process (thinning-out process) and an intensity interpolation process for every M or N pixels in the x direction and the y direction are performed on the normalized T-step fringe images to obtain M×N×T-step phase-shifted moiré fringe images represented by Expression (22).

Expression 22

$$\bar{I}_{moire}(x, y; m, n, t) = \\ \cos\left\{2\pi\left(\frac{1}{P} - \frac{1}{M}\right)x + 2\pi\left(\frac{1}{Q} - \frac{1}{N}\right)y + \varphi_0(x, y) + 2\pi\frac{m}{M} + 2\pi\frac{n}{N} + \\ 2\pi\frac{t}{T}\right\} = \cos\left\{\varphi_{moire}(x, y) + 2\pi\frac{m}{M} + 2\pi\frac{n}{N} + 2\pi\frac{t}{T}\right\}$$ (22)

In Expression (22), 2πm/M means a spatial phase-shift in the x direction, 2πn/N means a spatial phase-shift in the y direction, and 2πt/T means a temporal phase-shift. Three-dimensional discrete Fourier transform, which is a process 65 related to variables m, n, and t in Expression (22), is applied to calculate the angle of deviation of a component with a frequency 1. In this way, the phase distribution of the moiré fringe is obtained by the following expression.

Expression 23

$$\bar{\varphi}_{moire}(x, y) = \\ -\arctan\frac{\sum_{m=0}^{M-1}\sum_{n=0}^{N-1}\sum_{i=0}^{T-1}\bar{I}_{moire}(x, y; m, n, t)\sin(2\pi n/M + 2\pi n/N + 2\pi t/T)}{\sum_{m=0}^{M-1}\sum_{n=0}^{N-1}\sum_{i=0}^{T-1}\bar{I}_{moire}(x, y; m, n, t)\cos(2\pi n/M + 2\pi n/N + 2\pi t/T)}$$ (23)

As shown in Expression (26), the phase distribution of the original grating represented by Expression (24) can be calculated by adding the phase distribution of each sampling point in the x direction and the y direction in a thinning-out process, which is a process 66, to the phase distribution of the moiré fringe represented by Expression (25).

Expression 24

$$\bar{\varphi}(x,y)$$ (24)

Expression 25

$$\bar{\varphi}_{moire}(x,y)$$ (25)

Expression 26

$$\bar{\varphi}(x, y) = \bar{\varphi}_{moire}(x, y) + 2\pi\frac{x}{M} + 2\pi\frac{y}{N}$$ (26)

EXAMPLE 4

Hereinbelow, embodiments of the present invention will be described in detail with reference to the accompanying drawings.

Figure 7:
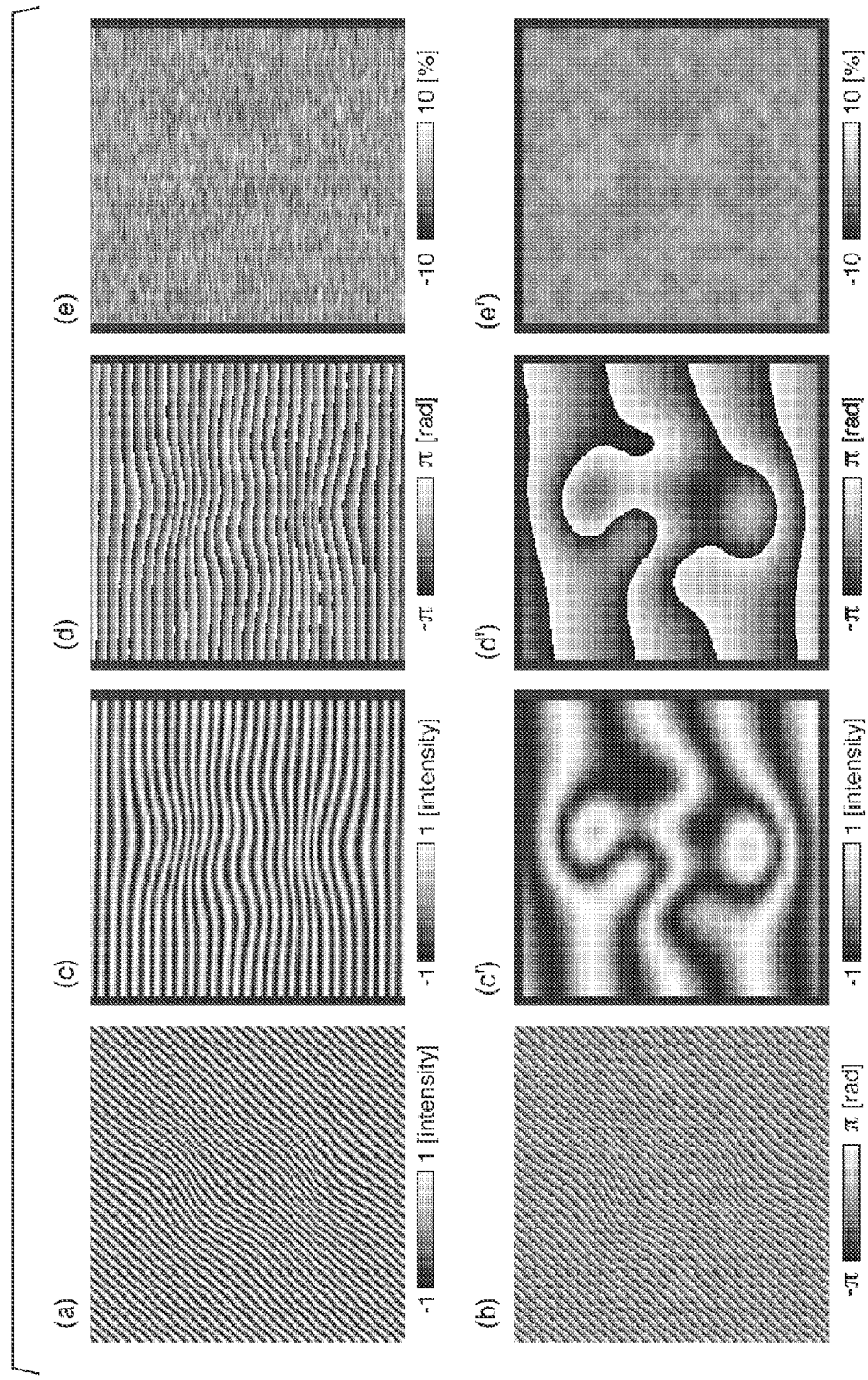
FIG. 7 is a diagram illustrating fringe images which are error comparison simulation results when random noise (SNR=3) is added.

First Embodiment: Improvement of Accuracy of Phase Analysis for Random Noise by Simulation FIG. 7 shows the result of a simulation for verifying the improvement of the accuracy of two-dimensional phase analysis based on Example 1 of the present invention, as compared to a one-dimensional sampling moiré method according to the related art. FIG. 7(a) shows a fringe image to be analyzed. In the fringe image, a grating has an intensity of amplitude of 75 and random noise with a standard deviation of 25 is added. In this case, the SNR of the fringe image corresponds to 3. FIG. 7(b) shows the ideal phase distribution of the fringe image shown in FIG. 7(a). FIG. 7(c) shows a moiré fringe image (a first image among eight phase-shifted images) according to the related art which is obtained by a thinning-out process and an intensity interpolation process for every eight pixels only in the x direction in FIG. 7(a). FIG. 7(d) shows the phase distribution of the moiré fringe shown in FIG. 7(c) which is obtained by the method according to the related art. FIG. 7(e) shows the phase error distribution of the one-dimensional sampling moiré method according to the related art. The average value of the phase errors in the entire evaluation region was 0.012% and a standard deviation was 2.18%.

Figure 8:
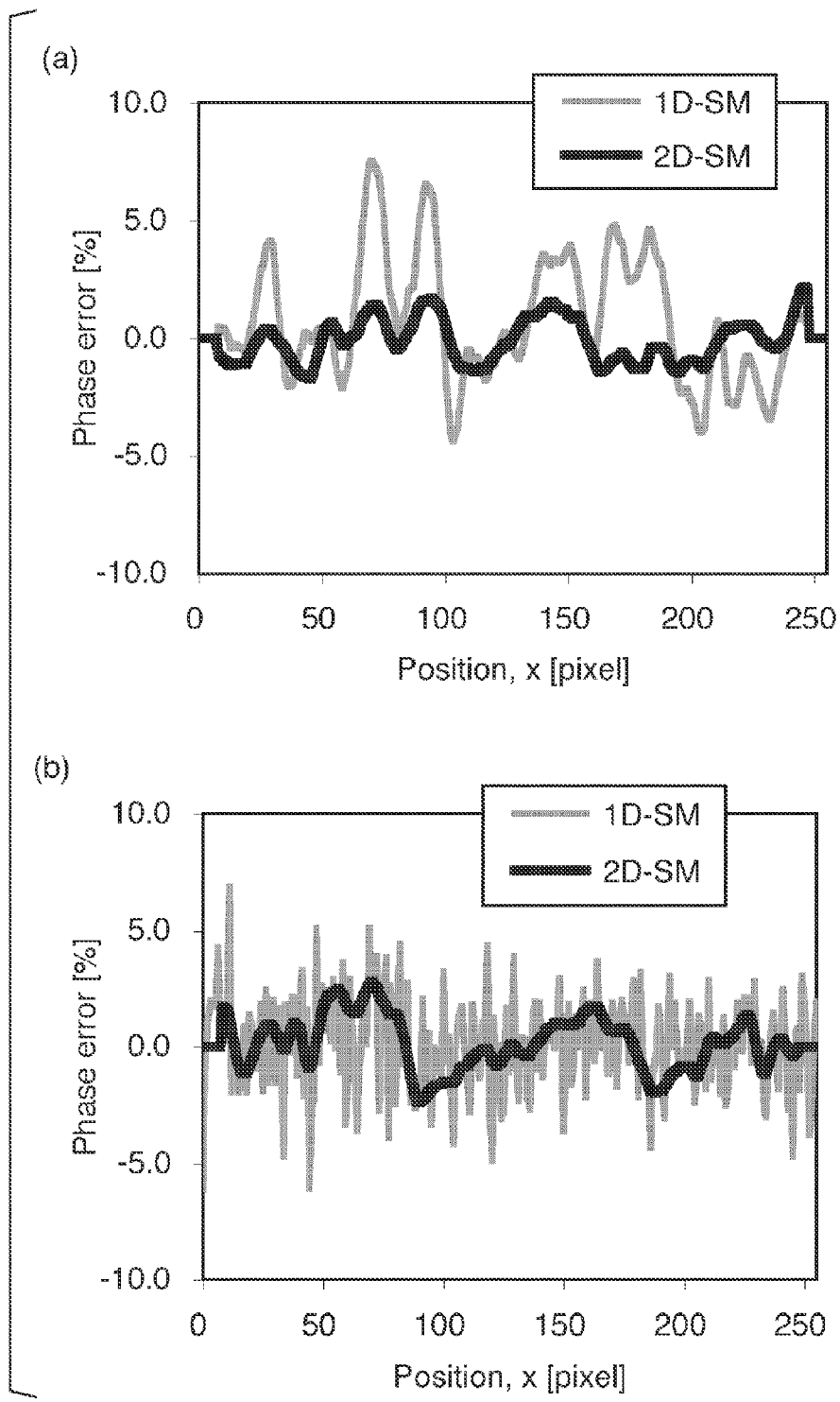
FIG. 8 is a diagram illustrating error comparison when random noise is added: the phase error of the pixel position of cross-sectional data of one line at the center in the x direction (a) and the y direction (b) in FIG. 7(e) and FIG. 7 (e').

FIG. 7(c') shows a moiré fringe image (a first phase-shifted image among 64 (=8×8) phase-shifted images) according to the present invention which is obtained by a thinning-out process and an intensity interpolation process performed for every eight pixels in the x and y directions in FIG. 7(a). FIG. 7(d') shows the phase distribution of the moiré fringe shown in FIG. 7(c') obtained by the present invention and FIG. 7(e')

shows a phase error distribution obtained by analysis in the present invention. The average value of the phase error in the entire evaluation region was 0.006% and the standard deviation was 0.84%. FIG. 8 shows the cross-sectional data of one line at the center in the x direction and the y direction in FIG. 7(*e*) and FIG. 7 (e'). As can be seen from the simulation results shown in FIGS. 7 and 8, it is possible to reduce a variation in the phase error, as compared to the method according to the related art.

Figure 9:
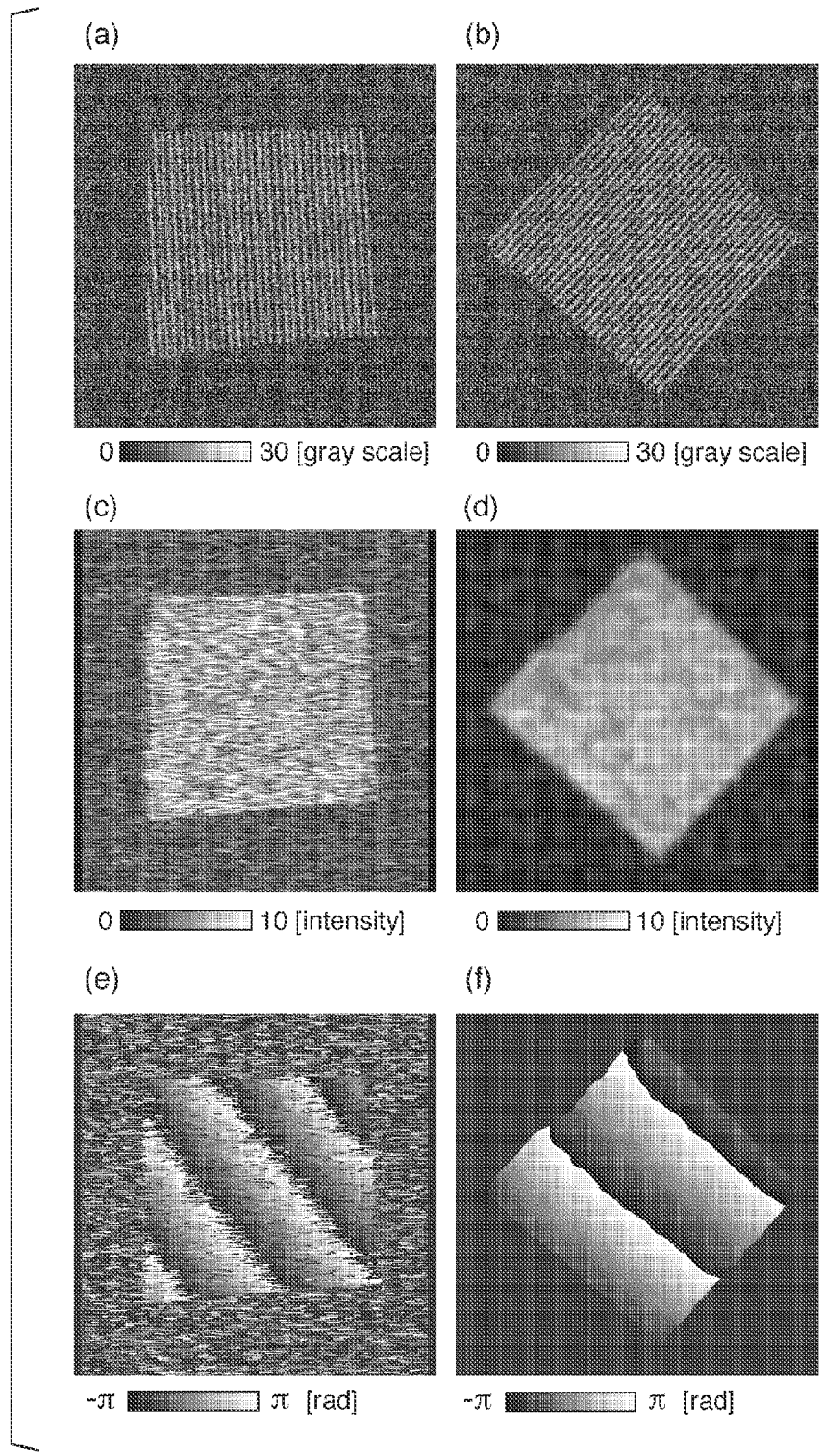
FIG. 9 is a diagram illustrating the experiment analysis result of a fringe grating in one direction.

Second Embodiment: Verification of Improvement of Accuracy of Phase Analysis for Fringe Grating Image in One Direction by Experiment In order to verify the validity of the method according to Example 1 of the present invention, the effect of the method was verified by the actual experiment. FIG. 9 shows a row of experiment results of Example 1. FIG. 9(*a*) shows a captured fringe image (image size is 500 pixels×500 pixels) of the surface of an object with a size of 30 mm square to which a sine wave with a grating pitch of 1.13 mm is attached. In this case, the exposure time of a CCD camera is 1/1000 and the aperture of a camera lens is F8. Therefore, the SNR of the captured fringe image is very low. FIG. 9(*b*) shows a fringe image which is acquired under the same imaging conditions, with the same object intentionally inclined at 45° in the inclination direction.

FIG. 9(*c*) shows the intensity of amplitude distribution of a moiré fringe which is obtained by one-dimensional analysis (the number of thinning-out processes M is 12) according to the related art and FIG. 9(*d*) shows the intensity of amplitude of a moiré fringe obtained by two-dimensional analysis (the numbers of thinning-out processes M and N are 16 and 15, respectively) according to Example 1 of the present invention. FIG. 9(*e*) shows the phase distribution of the moiré fringe obtained by the one-dimensional analysis (the number of thinning-out processes M is 12) according to the related art and FIG. 9(*f*) is the phase distribution of the moiré fringe obtained by the two-dimensional analysis (the numbers of thinning-out processes M and N are 16 and 15, respectively) according to Example 1 of the present invention. In a black portion in FIGS. 9(*e*) and 9(*f*), a pixel in which the amplitude of the moiré fringe is equal to or less than 2.5 in FIGS. 9(*c*) and 9(*d*) is masked in black. As can be seen from FIG. 9, even though the imaging conditions and the number of captured images are the same, the analysis accuracy of the phase distribution in the present invention is higher than that in the related art.

Figure 10:
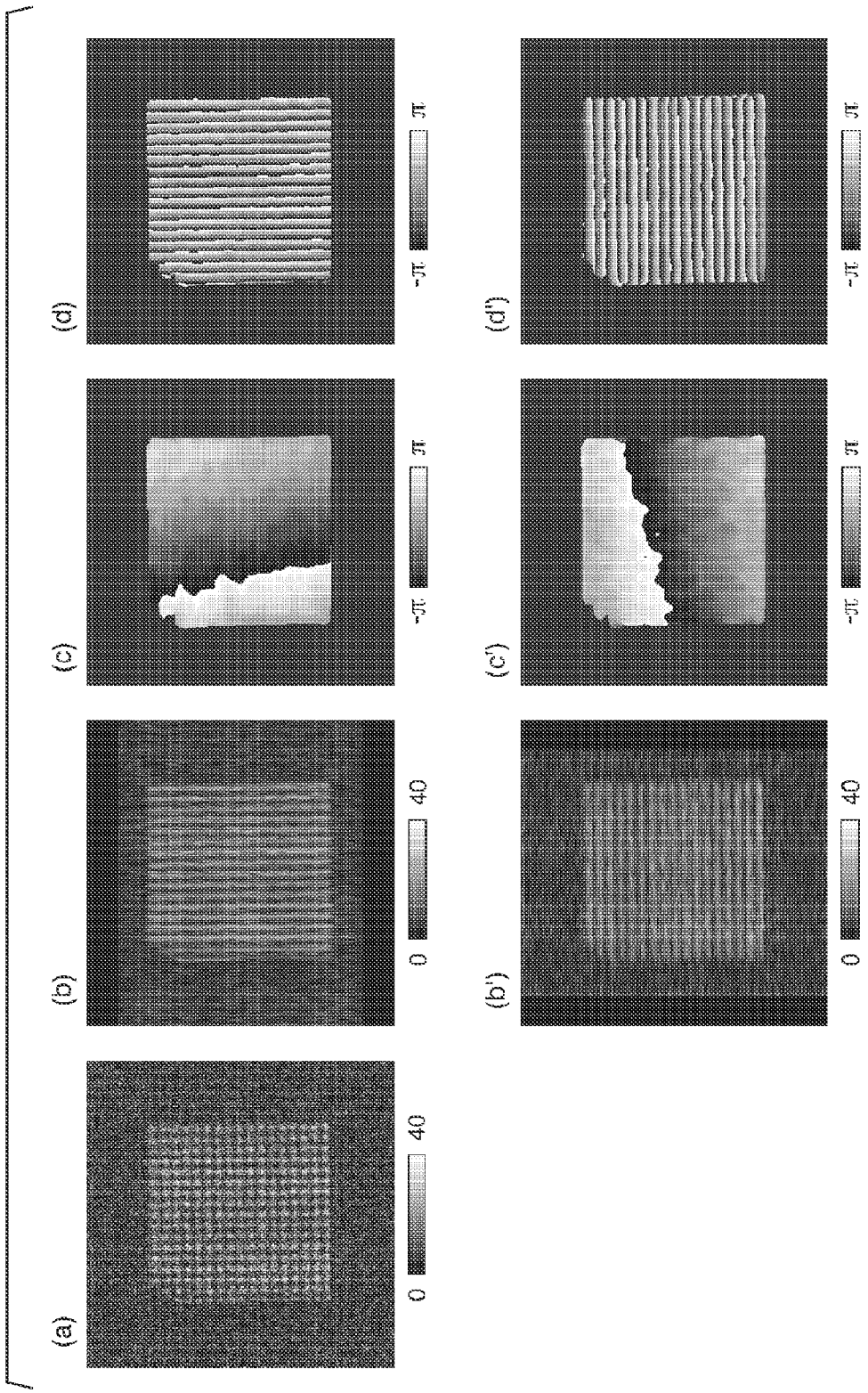
FIG. 10 is a diagram illustrating the experiment analysis result of a fringe grating in two directions by the one-dimensional sampling moiré method.
Figure 11:
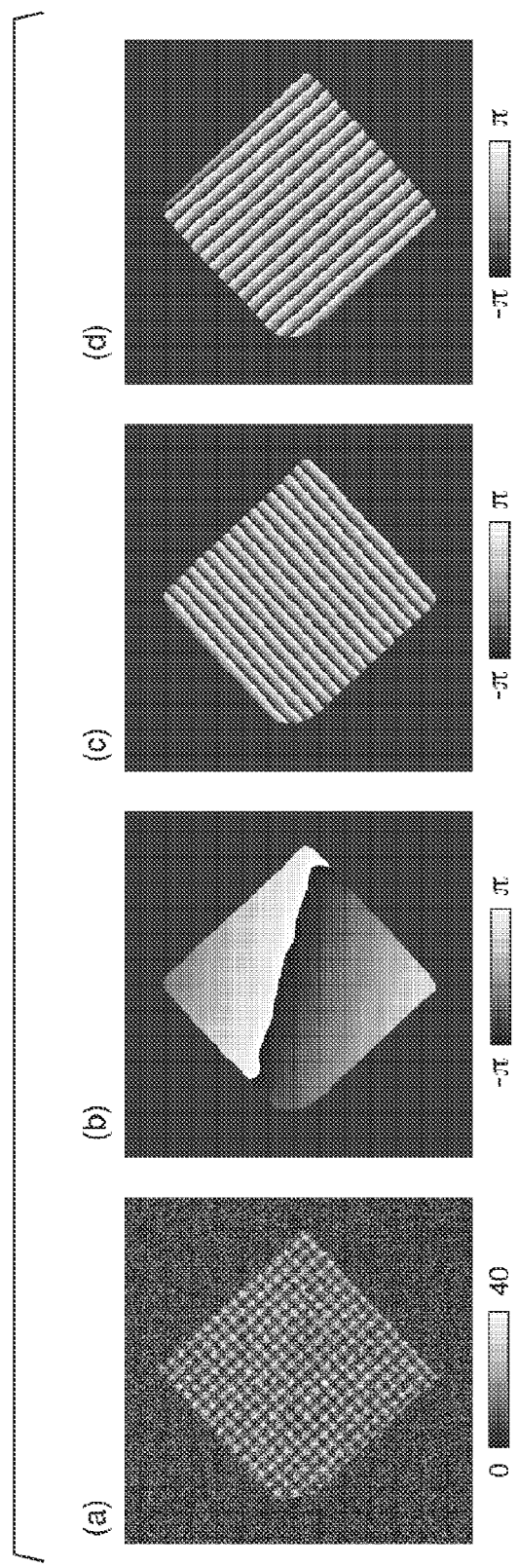
FIG. 11 is a diagram illustrating the experiment analysis result of a fringe grating in two directions by the two-dimensional sampling moiré method.

Third Embodiment: Verification of Improvement of Accuracy of Simultaneous Phase Analysis for Fringe Grating Image in Two Directions by Experiment FIGS. 10 and 11 show the experiment results for verifying the improvement of the accuracy of simultaneous phase analysis for a fringe image in two directions in the method according to Example 1 of the present invention. FIG. 10 shows the analysis result of the experiment by the method according to the related art. FIG. 10(*a*) shows a captured two-dimensional fringe image (an image size of 400 pixels× 400 pixels) of the surface of an object with a size of 30 mm square to which a two-dimensional sine wave with a grating pitch of 1.13 mm is attached. In this case, the exposure time of the CCD camera is 1/1000 and the aperture of the camera lens is F8. Therefore, the SNR of the captured fringe image is very low. FIG. 10(*b*) and FIG. 10(*b'*) show grating images in the x direction and the y direction which are separated by a low-pass filtering process, respectively. FIG. 10(*c*) and FIG. 10(*c'*) show the phase distributions of the moiré fringes in the x direction and the y direction which are obtained by a one-dimensional sampling moiré method (the number of thinning-out processes M is 12), respectively. FIG. 10(*d*) and FIG. 10(*d'*) show the phase distributions of the finally obtained fringe images in the x direction and the y direction, respectively. The one-dimensional sampling moiré method according to the related art performs a low-pass filtering process on one two-dimensional fringe grating, separates the fringe gratings in the x direction and the y direction, and calculates phase distributions in two directions. Therefore, the method can be applied to, for example, the measurement of two-dimensional in-plane displacement. However, since SNR is low, a lot of errors are included in the measurement result.

FIG. 11 shows the analysis result of the experiment according to the present invention. FIG. 11(*a*) shows a fringe grating image which is captured when the same object as that shown in FIG. 10(*a*) is inclined at 45° in the inclination direction. FIG. 11(*b*) shows the phase distribution of a moiré fringe which is obtained by applying the two-dimensional sampling moiré method (the numbers of thinning-out processes M and N are 16 and 15, respectively) to FIG. 11(*a*) and is calculated by two-dimensional DFT according to the present invention. FIGS. 11(*c*) and 11(*d*) show phase distributions in two directions which are obtained by adding the phase distribution of the number of thinning-out processes in the x direction or the y direction to the phase distribution shown in FIG. 11(*b*). The two-dimensional sampling moiré method according to the present invention can simultaneously calculate the phase distributions in two directions, without performing a low-pass filtering process on one two-dimensional grating. In addition, since the method is resistant to random noise, the result with few errors is obtained and it is possible to confirm the effect of the present invention.

Fourth Embodiment: Influence of Random Noise by Simulation

Figure 12:
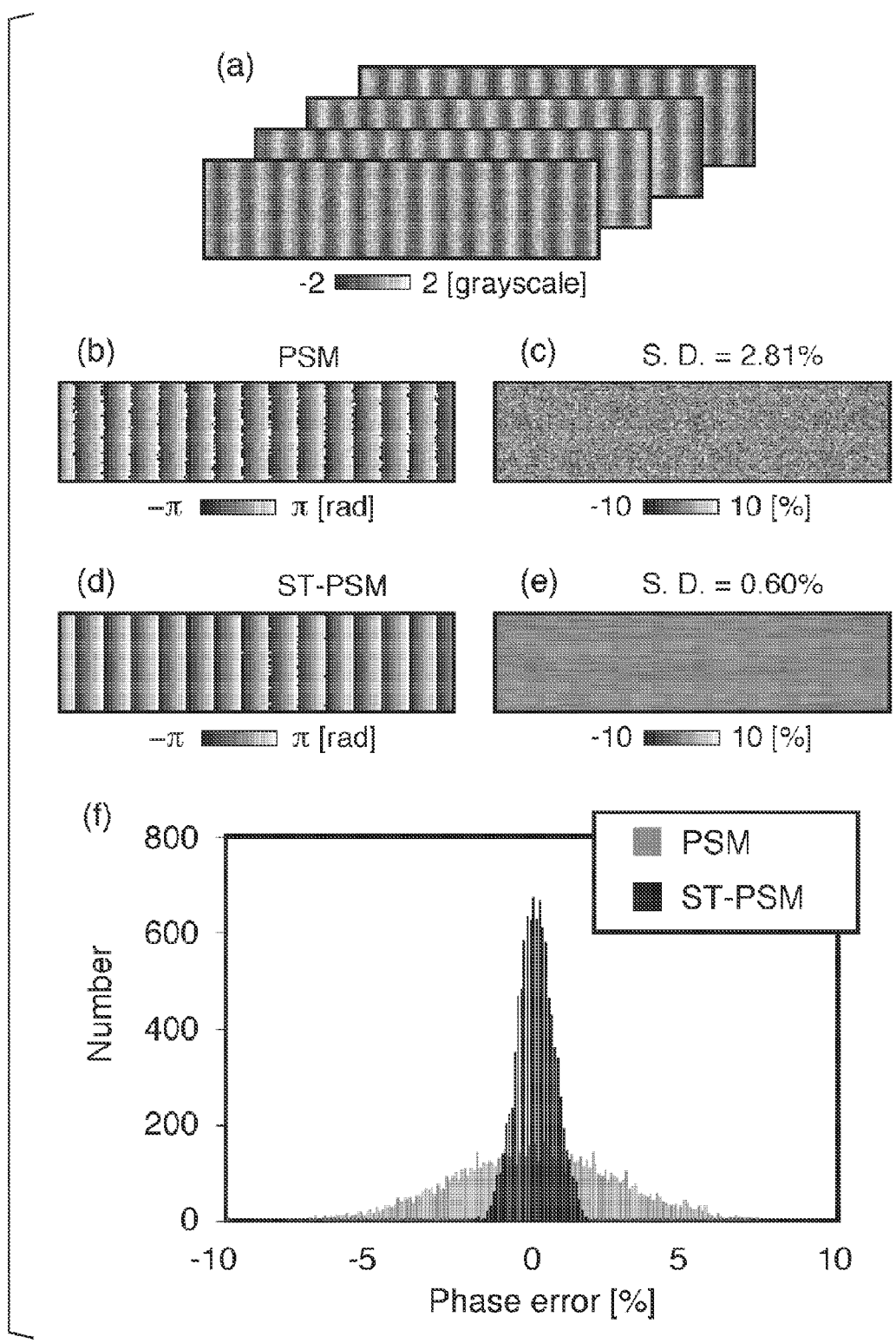
FIG. 12 is a diagram illustrating the comparison between phase errors due to random noise generated by a simulation.

FIG. 12 shows the simulation result when random noise is added in order to verify the validity of the method according to Example 2 of the present invention. In the simulation, four phase-shifted sine waves having a grating pitch of 14.1 pixels were made and an image obtained by adding random noise with a standard deviation of 25% to each grating image was used. In an image size of 256 pixels×256 pixels, a central region of 200 pixels×50 pixels was evaluated.

FIG. 12(*a*) shows four phase-shifted fringe grating images. FIGS. 12(*b*) and FIG. 12(*d*) show phase distributions which are obtained by a phase shifting method (PSM) according to the related art and a two-dimensional spatiotemporal phase shifting method (ST-PSM) (the number of thinning-out processes M is 14) according to Example 2 of the present invention, respectively. FIGS. 12(*c*) and 12(*e*) show error distributions which are obtained by the phase shifting method according to the related art and the two-dimensional spatiotemporal phase shifting method according to Example 2 of the present invention, respectively. FIG. 12(*f*) shows a histogram illustrating the phase error distributions of the two methods. While the standard deviation of the phase error is 2.81% in the method according to the related art, a variation in the phase error can be significantly reduced to 0.6% in the method according to the present invention.

Figure 21:
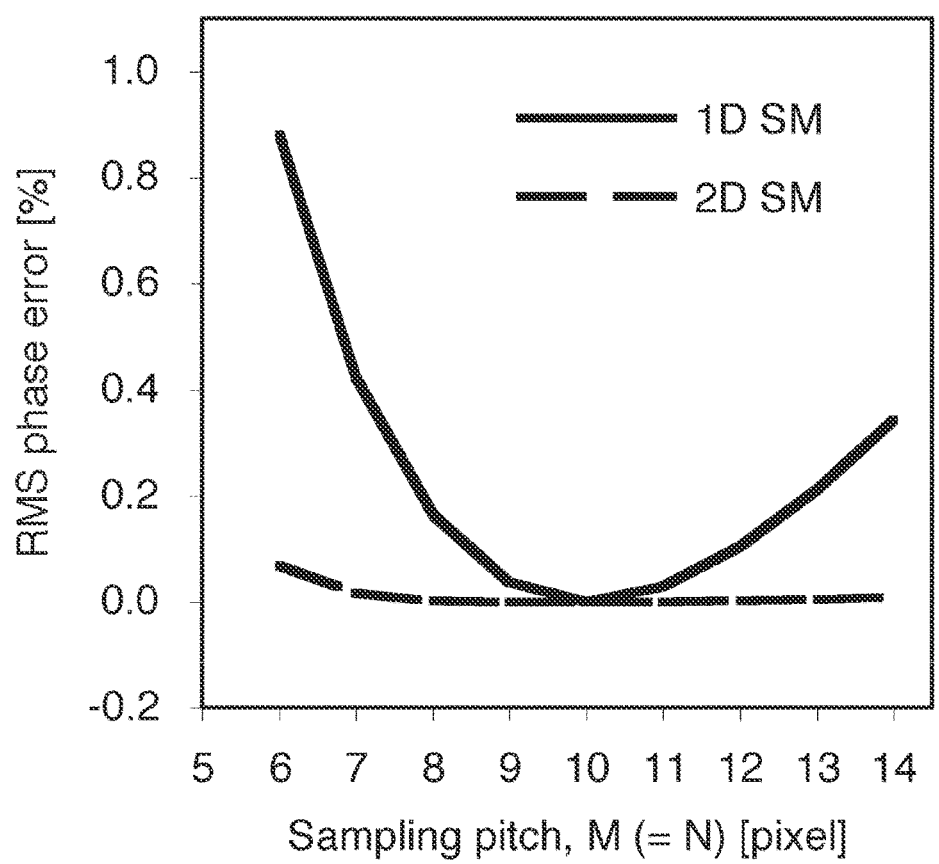
FIG. 21 is a diagram illustrating the relationship between the number of thinning-out processes and a phase error by a simulation (a solid line indicates the analysis result obtained by a one-dimensional sampling moiré method according to the related art and a dashed line indicates the analysis result obtained by a two-dimensional sampling moiré method according to the present invention).

Moreover, FIG. 21 shows the result of a simulation for the influence of an analysis error due to a difference in the number of thinning-out processes during analysis in the two-dimensional sampling moiré method (two-dimensional spatial analysis method) which is the first method.

In the simulation, first, a one-dimensional sine wave image (150 pixels×150 pixels) having a grating pitch of 10 pixels in the x direction was created and analysis conditions were changed such that the number of thinning-out processes M in the x direction was changed from 6 pixels to 14 pixels under the conditions that no noise was added. Then, phase analysis was performed by the one-dimensional sampling moiré method according to the related art and the value (a portion indicated by a solid line in FIG. 21) of the root-mean-square of the difference from the logical phase distribution in a central evaluation region (100 pixels×100pixels) was plotted. Then, a one-dimensional inclined sine wave having a grating pitch of 10 pixels in the x direction and the y direction was created and analysis conditions were changed such that the number of thinning-out processes (M=N) in the x direction and the y direction was changed from 6 pixels to 14 pixels under the conditions that no noise was added. Then, phase analysis was performed by the first method according to the present invention and the value (a portion indicated by a dashed line in FIG. 21) of the root-mean-square of the difference from the logical phase distribution was plotted.

As shown in FIG. 21, in the one-dimensional sampling moiré method according to the related art, only when the number of thinning-out processes is completely identical to the original grating pitch, a (periodic) error does not occur. When the original grating pitch is not identical to the number of thinning-out processes, a large error occurs. In contrast, according to the present invention, even when the original grating pitch is not identical to the number of thinning-out processes, little error occurs. This means that the accurate number of thinning-out processes is not determined during analysis and high-accuracy phase analysis is performed in the present invention. This effect is the same as that in the spatiotemporal phase shifting method (two-dimensional spatiotemporal analysis), which is the second method, and the spatiotemporal phase shifting method (three-dimensional spatiotemporal analysis), which is the third method.

Fifth Embodiment: Influence of Vibration by Simulation

Figure 13:
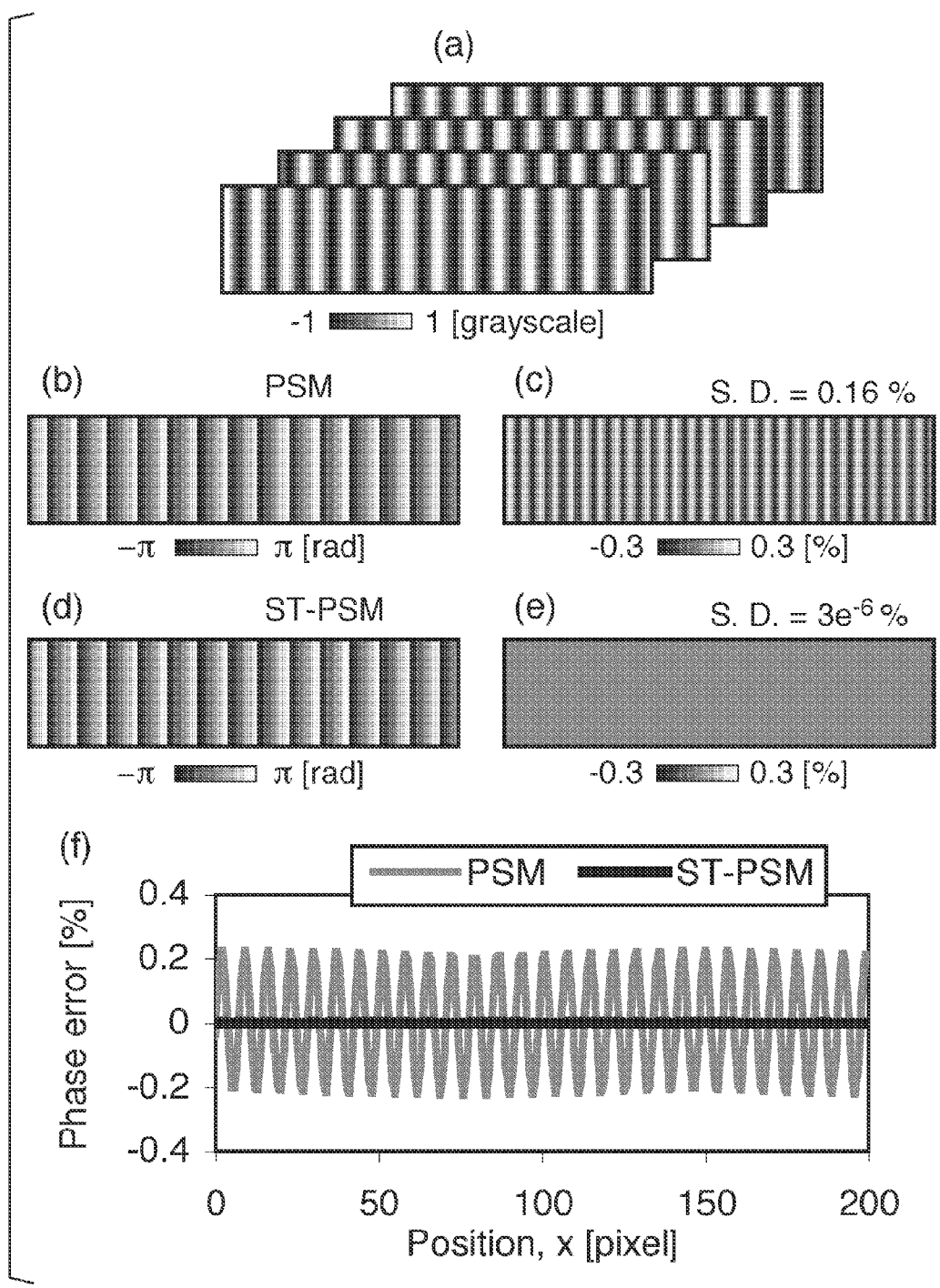
FIG. 13 is a diagram illustrating the comparison between phase errors due to vibration (phase-shift error) generated by a simulation.

FIG. 13 shows the simulation result when a phase-shift error is given by, for example, vibration in order to confirm the validity of the method according to Example 2 of the present invention. In the simulation, an image obtained by respectively giving phase-shift errors of $-\pi/10$, $-\pi/15$, $\pi/10$, and $\pi/15$ to four phase-shifted sine waves having a grating pitch of 14.1 pixels was used. In an image size of 256 pixels× 256 pixels, a central portion with a size of 200 pixels×50 pixels was evaluated. FIG. 13(a) shows four phase-shifted fringe grating images.

FIGS. 13(b) and 13(d) show phase distributions which are obtained by the phase shifting method (PSM) according to the related art and the two-dimensional spatiotemporal phase shifting method (ST-PSM) (the number of thinning-out processes M is 14) according to Example 2 of the present invention, respectively. FIGS. 13(c) and 13(e) show error distributions which are obtained by the phase shifting method according to the related art and the two-dimensional spatiotemporal phase shifting method according to Example 2 of the present invention, respectively. FIG. 13(f) shows the cross-sectional data of one horizontal line at the center in the phase error distribution shown in FIGS. 13(c) and 13(e). As can be seen from FIG. 13(f), when a phase-shift error occurs without random noise, a periodic phase error occurs in the phase shifting method according to the related art. In contrast, the present invention is little affected by vibration.

Figure 14:
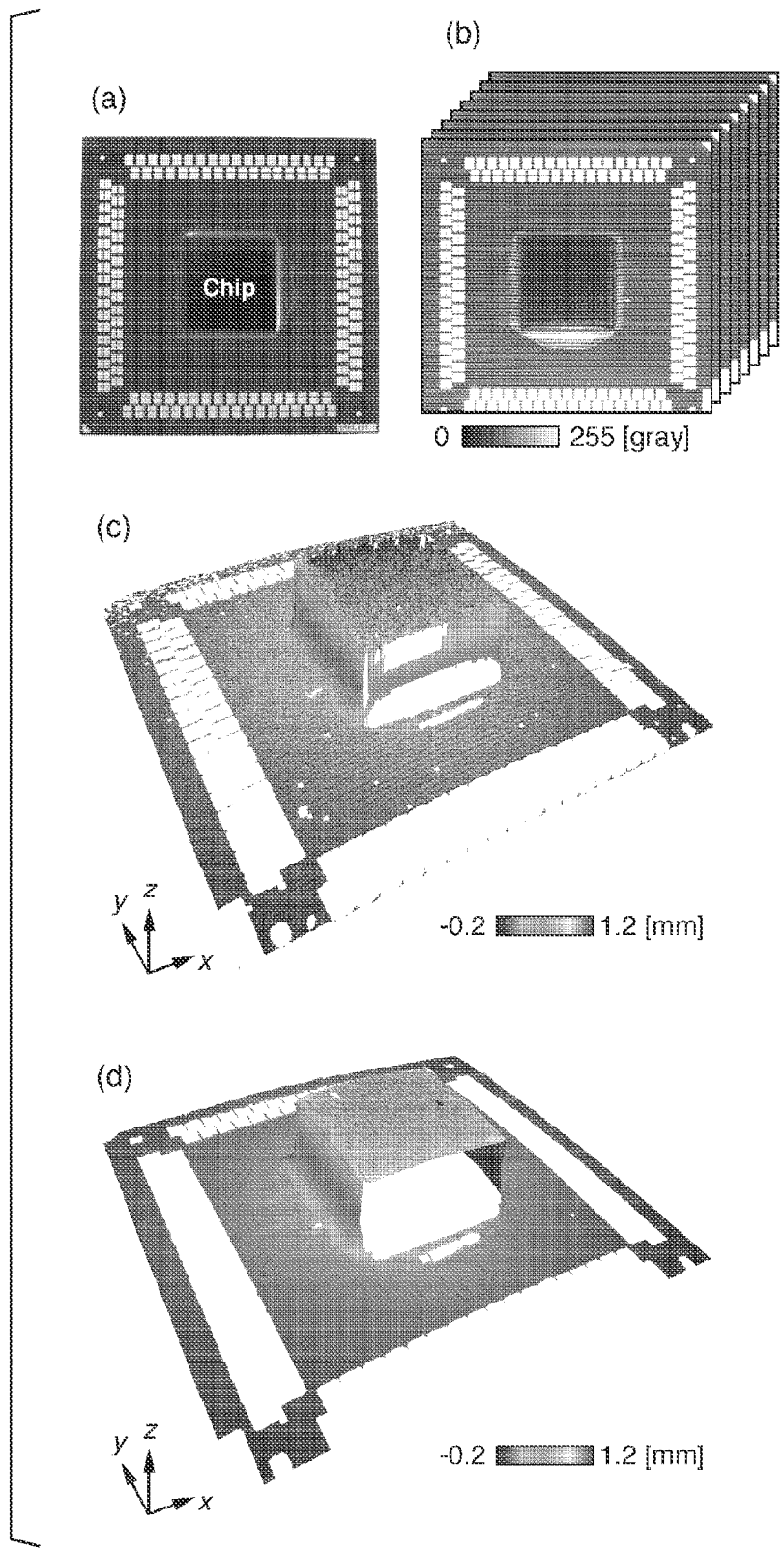
FIG. 14 is a diagram illustrating the measurement result of the warpage distribution of a semiconductor package to which a grating projection method is applied.

Sixth Embodiment: Measurement of Warpage Distribution of Semiconductor Package by Experiment FIG. 14 shows the result of an experiment for applying a fringe image phase analysis method to a grating projection method and measuring the warpage distribution of a semiconductor package (FC-BGA) in order to verify the validity of the method according to Example 2 of the present invention. In the grating projection method, when a grating pattern is projected onto the surface of the object to be measured by a projector or the like and is observed by cameras which are provided at different angles and positions, the projected grating is distorted depending on the height of the object. Phase analysis can be performed on the amount of distortion to measure the height (warpage) of the object.

FIG. 14(a) shows a semiconductor package (size: 50 mm×50 mm) which is the object to be measured. FIG. 14(b) shows eight captured phase-shifted fringe images. FIGS. 14(c) and 14(d) show warpage distributions which are obtained by an 8-step phase-shift according to the related art and the present invention, respectively. In a chip portion which is provided at the center of the sample, reflectance is low. Therefore, in the measurement result by the phase shifting method according to the related art, a large variation (measurement is partially unavailable) occurs. In addition, a periodic error occurs in the measurement result of the entire sample due to a phase-shift error which is caused by the influence of vibration in a measurement environment. In contrast, according to the present invention, in the chip portion with low reflectance or the entire sample, the warpage distribution with few errors is obtained. It is possible to confirm the effect of the present invention.

Seventh Embodiment: Comparison of Influence of Random Noise by Simulation

Figure 15:
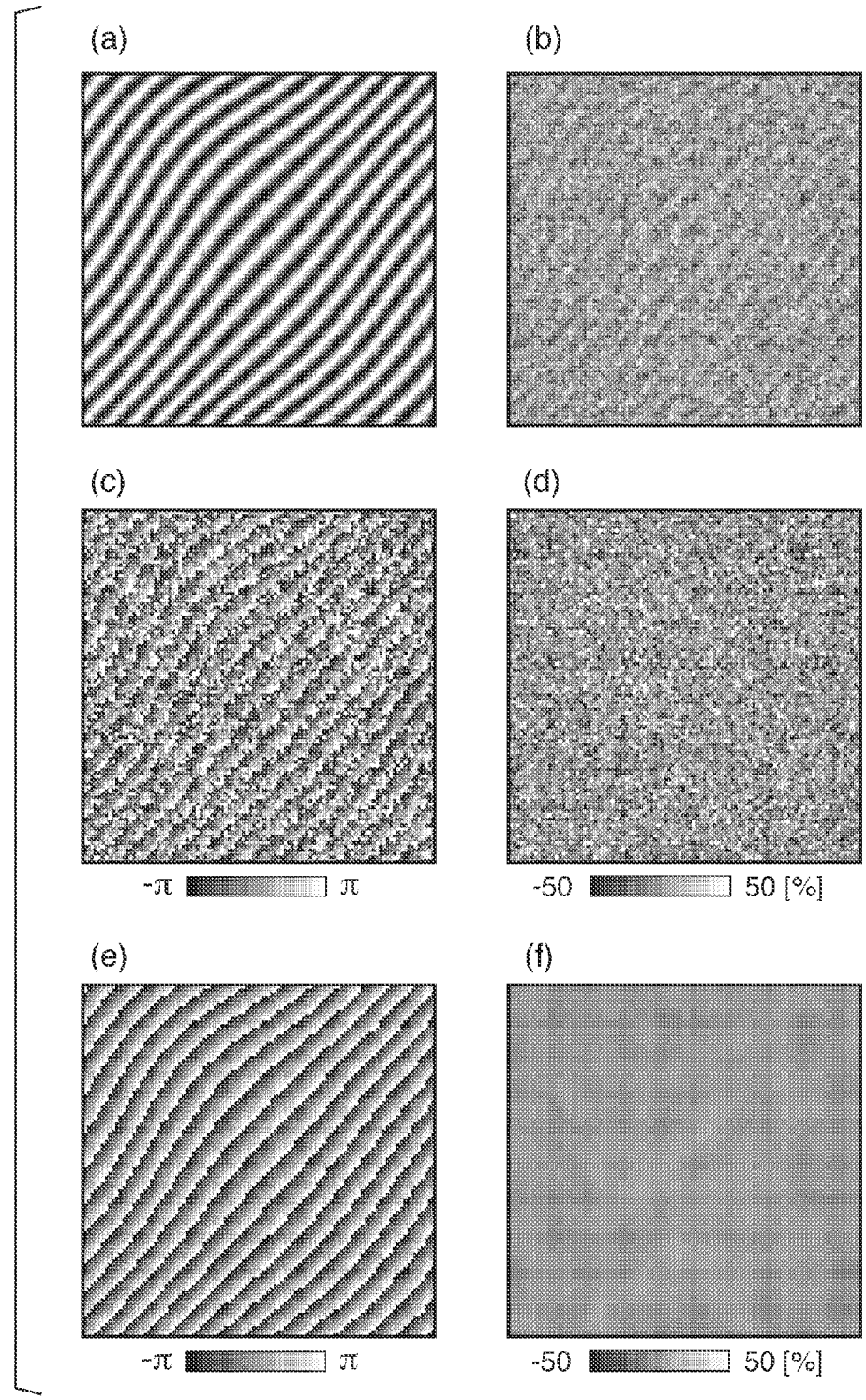
FIG. 15 is a diagram illustrating the simulation result when a random noise level of 200% is added.
Figure 16:
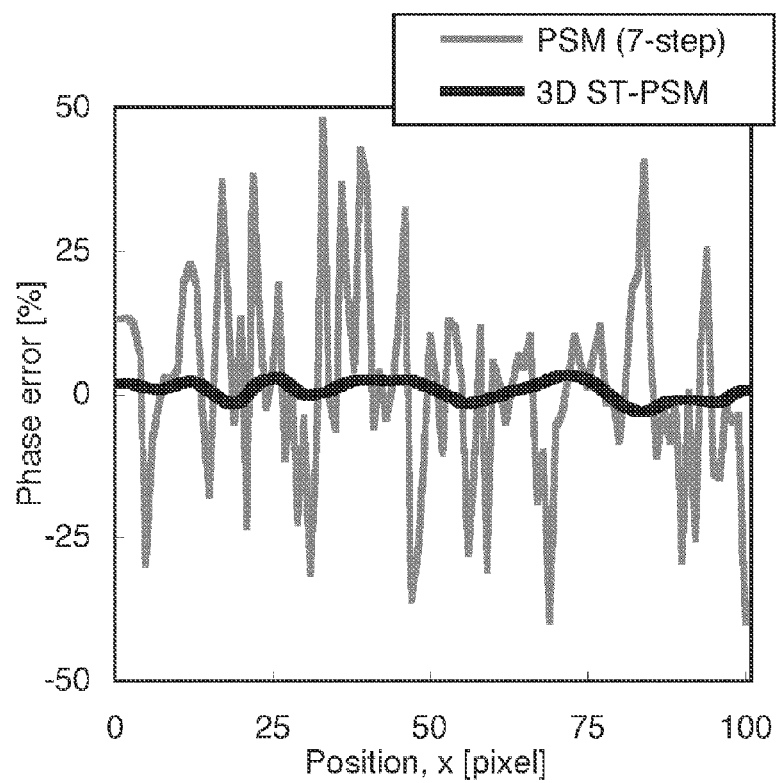
FIG. 16 is a diagram illustrating the comparison between the phase errors of the pixel position of the cross-sectional data of one line at the center in the x direction of FIGS. 15(d) and 15(f).

FIGS. 15 and 16 show the simulation results when random noise is added in order to verify the validity of the method according to Example 3 of the present invention. FIG. 15(a) shows an ideal inclined fringe image to be analyzed without random noise. Here, among seven phase-shifted fringe images, only the first phase-shifted fringe image is shown. FIG. 15(b) shows the fringe image obtained by adding random noise with a standard deviation of 200% to the fringe image shown in FIG. 15(a). In FIG. 15(b), among seven phase-shifted fringe images, only the first phase-shifted fringe image is shown. In this case, the SNR of the fringe image corresponds to 0.5. FIGS. 15(c) and 15(d) show a phase distribution and an error distribution which are obtained by a 7-step phase shifting method according to the related art. As can be seen from FIG. 15(d), since a noise component doubles the signal component to be analyzed, it is difficult to analyze the signal component using the method according to the related art.

FIGS. 15(e) and 15(f) show a phase distribution and an error distribution which are obtained by a three-dimensional spatiotemporal phase shifting method (the numbers of thinning-out processes M and N are 8 and the number of phase-shifts T is 7) according to the present invention. In the entire image shown in FIG. 15(f), the standard deviation of the phase error was 1.71%. Even though measurement conditions were very bad, it was possible to calculate the phase distribution with an error of several percent or less which was difficult to measure in the related art. FIG. 16 shows the cross-sectional data of one line at the center in the x direction of FIGS. 15(e) and 15(f). The effect of the present invention is more remarkable than the measurement result of the method according to the related art.

EXAMPLE 5

The application field of the present invention which has been described in detail above will be described below. However, the application field is not limited thereto.

First, the present invention can be applied to the following: the high-accuracy three-dimensional shape measurement or quality management of electronic components in the electronic industry or molded products and processed products in the automobile industry; and the three-dimensional shape and displacement measurement of electronic components, die-molded products, or the like by a grating projection method, vehicle body shape inspection or dent detection, the production of custom-made clothes by the automatic measurement of the shape of a human body, and the storage of data for the three-dimensional shape of precious works of art, handicrafts, and unearthed articles in the general manufacturing industry or the garment industry.

Figure 17:
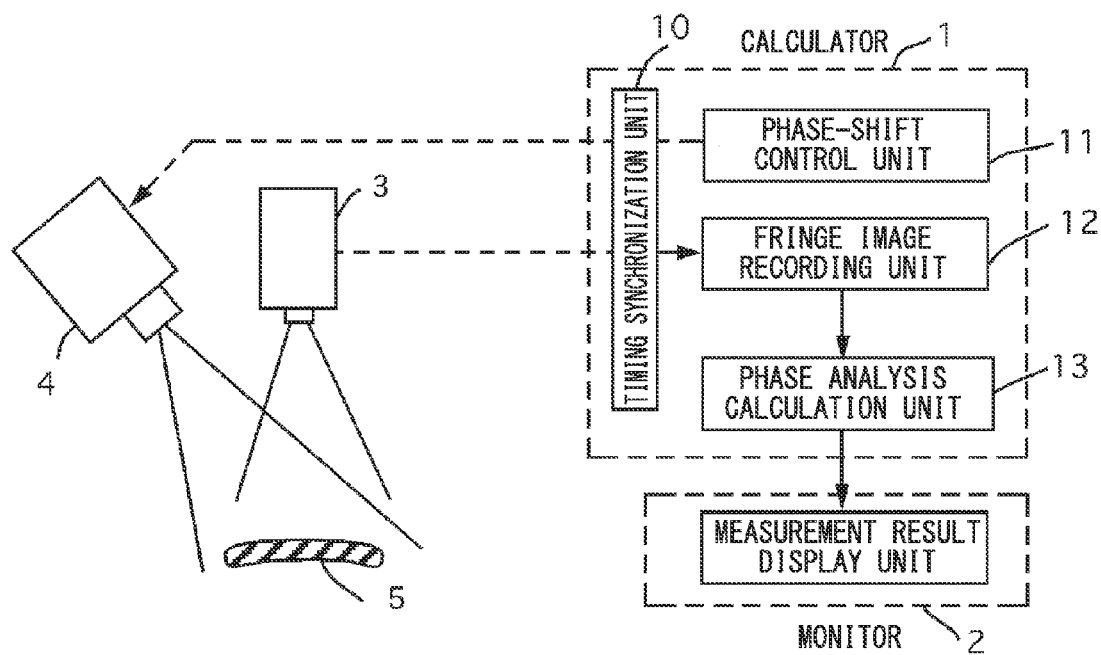
FIG. 17 is a diagram illustrating the structure of an example in which the present invention is applied to the measurement of the shape and deformation (out-of-plane displacement) of an object by the grating projection method.

FIG. 17 shows an example of a device using the grating projection method for measuring the three-dimensional shape of an object. However, the present invention is not limited thereto. A camera 3 captures a grating pattern which is projected onto the surface of a diffusing object, which is an object 5 to be measured, by a grating projection device 4. The captured grating pattern is distorted depending on the height of the object to be measured. Therefore, when calibration for investigating the relationship between a phase and a height in advance is performed on the phase-shift of a fringe image due to the distortion, it is possible to measure the height information of the object from the phase value of the fringe image. When a plurality of phase-shifted grating patterns are projected, a phase-shift control unit 11 in a calculator 1 sequentially projects the grating patterns with a slight phase-shift and a fringe grating image recording unit 12 acquires fringe image data in response to a signal from a timing synchronization unit 10. A phase analysis calculation unit 13 performs a fringe image phase distribution analysis method described in the above-mentioned example to calculate a phase distribution and outputs the measurement result of shape data to a monitor 2.

EXAMPLE 6

In the optical field, the present invention can be applied to the following: the accurate inspection of the thickness, flatness, parallelism, and the like of optical components by various types of interferometers (for example, a Michelson interferometer, a Mach-Zehnder interferometer, and a Fizeau interferometer) in structural evaluation by the observation and quantitative measurement of the refractive index distribution of optical switching elements, optical waveguides, optical fibers, and the like in the research, development, and manufacturing fields of optical devices; and structural evaluation by the quantitative measurement of the refractive index distribution or inclination angle of optical switching elements, optical waveguides, optical fibers, and the like in the research and development of optical devices.

Figure 18:
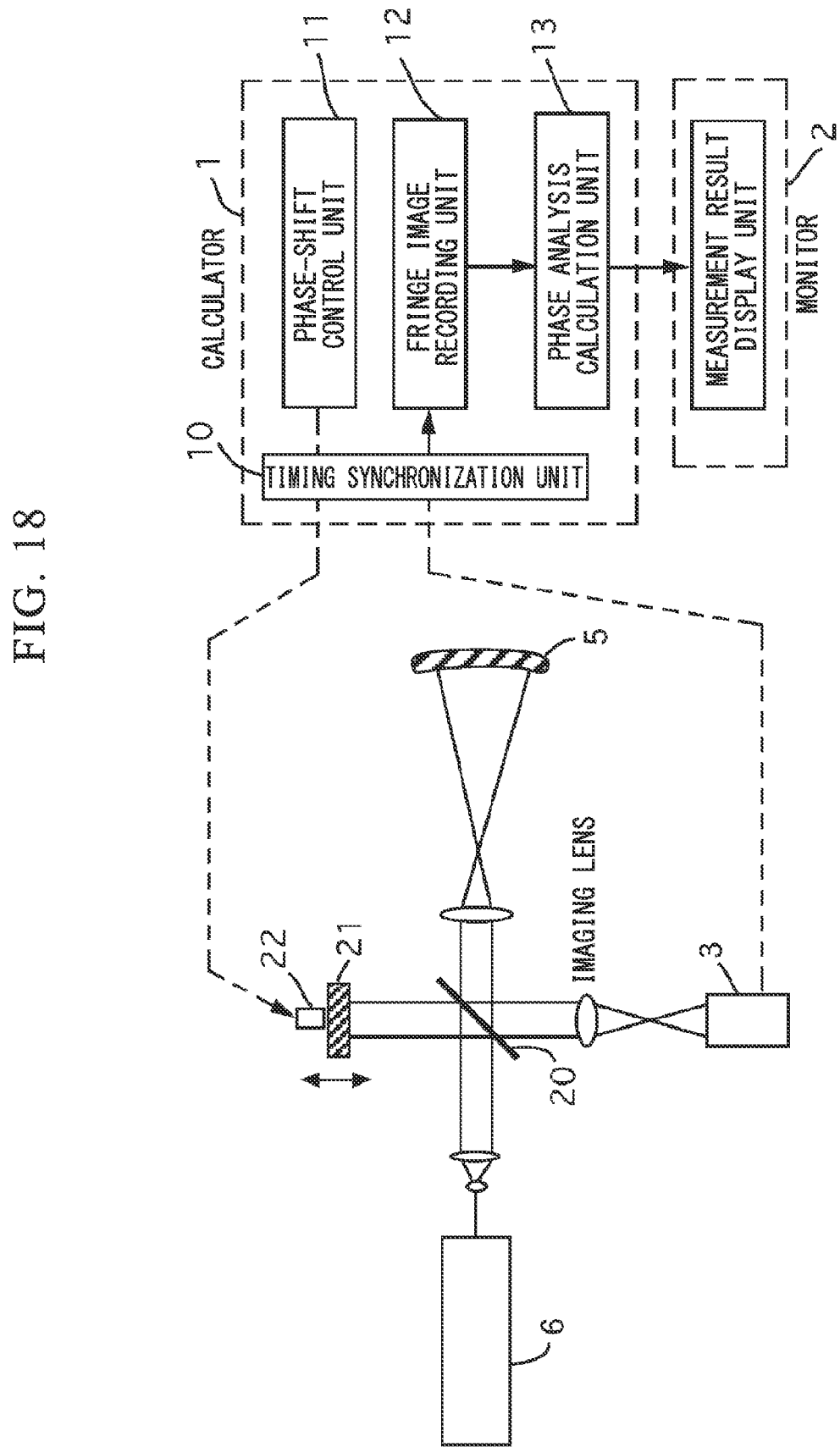
FIG. 18 is a diagram illustrating the structure of an example in which the present invention is applied to interference fringe analysis for measuring the surface shape of an optical component.

FIG. 18 shows an example of a device using a Twyman-Green interferometer for measuring the surface shape of an optical component, but the present invention is not limited thereto. A collimated laser beam from a laser 6 is radiated to a reference mirror 21 and an optical component, which is an object 5 to be measured, by a half mirror 20. Light reflected therefrom is incident on a camera 3 through the half mirror 20. The reference mirror 21 is slightly inclined in order to introduce a high-frequency carrier fringe to an interference pattern. In order to introduce a phase-shift, a PZT stage 22 may be used to move the reference mirror. The obtained interference fringe pattern is captured by the camera 3 and is input to a recording unit 12 of a calculator 1. A calculation unit 13 performs the fringe image phase distribution analysis method described in the above-mentioned example to calculate a phase distribution and outputs the evaluated measurement result to a monitor 2.

EXAMPLE 7

The present invention can be applied to the following in the civil engineering and construction field: the detection of the defects of an object by phase information about ultrasonic images; the detection of a landslide by detection of anomalous displacement; and, in the integrity evaluation of infrastructures, an increase in the lifespan of the infrastructures by non-destructive inspection evaluation (for example, the detection of defects by ultrasonic images or the measurement of a displacement and distortion distribution by grating images) and the detection of the sign of a sediment disaster by remote monitoring which installs a grating panel on a slope.

Figure 19:
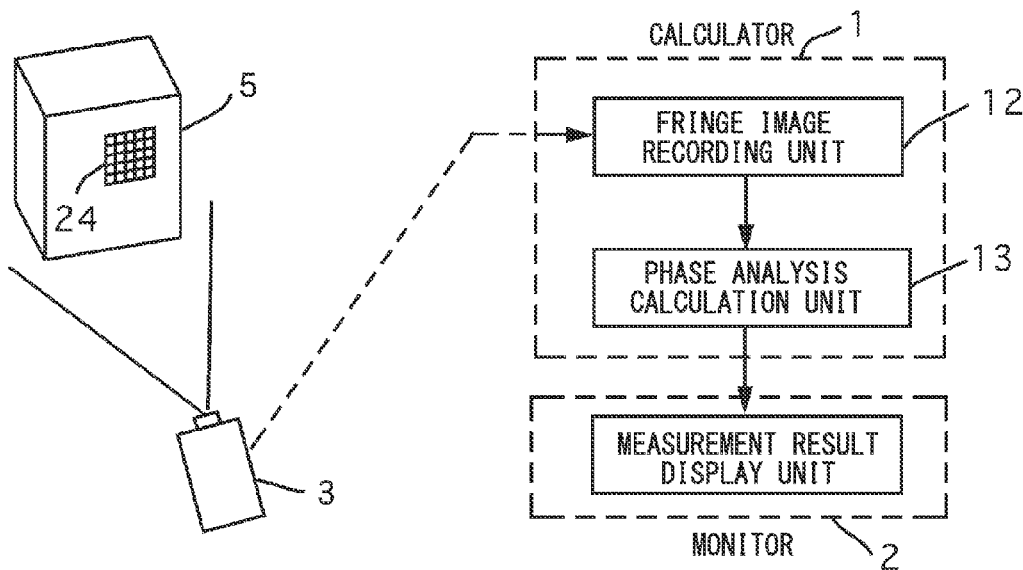
FIG. 19 is a diagram illustrating the structure of an example in which the present invention is applied to the measurement of the deformation of a structure using image measurement.

FIG. 19 shows an example of a device using image measurement for measuring the displacement distribution of a structure, but the present invention is not limited thereto. A grating pattern 24 is given to the surface of a structure which is an object 5 to be measured (for example, the attachment of a grating or the coating of a grating pattern). A time-series fringe grating image in a deformation process which is captured by a camera 3 which is a predetermined distance away from the object is input to a recording unit 12 of a calculator 1. A calculation unit 13 performs the fringe image phase distribution analysis method described in the above-mentioned example to calculate a phase distribution and outputs the measurement result of the evaluated displacement distribution to a monitor 2.

EXAMPLE 8

The present invention can be applied to an orthopedic or stone model database in non-invasive diagnosis or cell analysis by an OCT, X-rays, or a phase-shift laser microscope in the medical and medical treatment fields.

In addition, the present invention can be applied to the microstructural observation, quantitative measurement, and the like of achromatic living body related samples in the biotechnology field.

Figure 20:
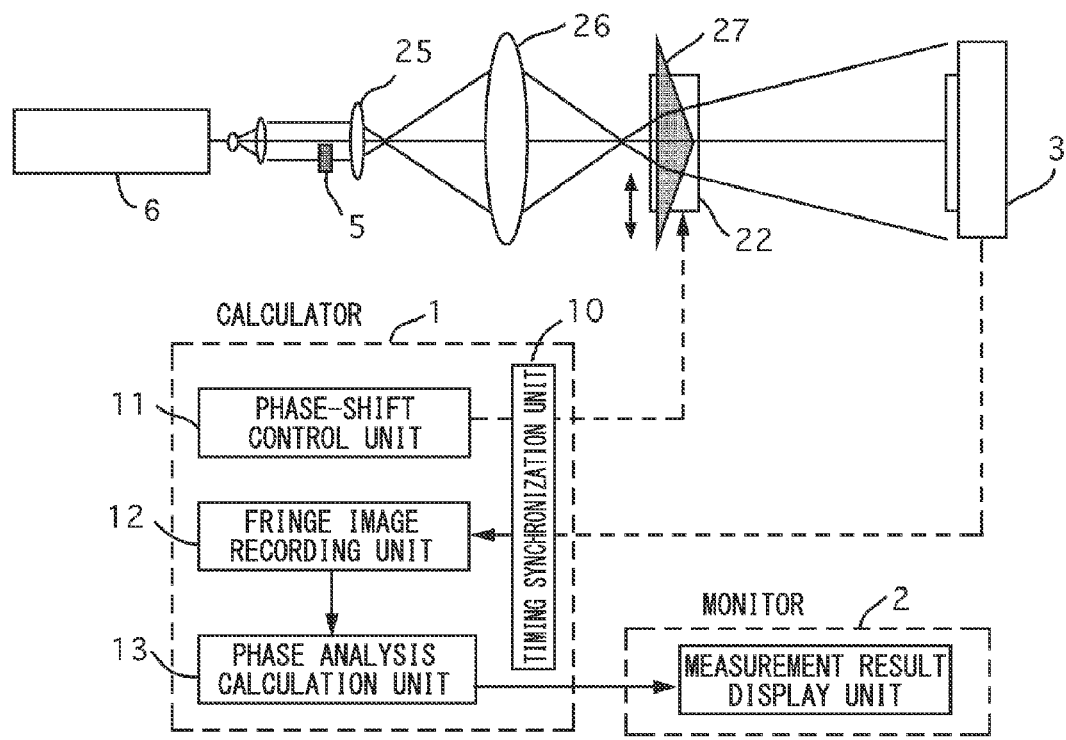
FIG. 20 is a diagram illustrating the structure of an example in which the present invention is applied to the measurement of the refractive index distribution of a living cell by a phase-shift laser microscope.

FIG. 20 shows an example of a device using a phase-shift laser microscope for measuring the refractive index distribution of a living cell, but the present invention is not limited thereto. In the phase-shift laser microscope, a magnifying lens 26 is arranged between an objective lens 25 and a biprism 27. For a collimated laser beam from a laser 6, a transparent object, which is an object 5 to be measured, is inserted into a portion corresponding to half of an incident plane wave and the remaining half is used as a reference wave. Object light which passes through the transparent object and reference light are refracted by the biprism 27 and overlap and interfere with each other on an observation surface of the camera 3. The biprism 27 is laterally moved by a PZT stage 22 to introduce a phase-shift and the fringe image captured by the camera 3 is input to a recording unit 12 of a calculator 1. A calculation unit 13 performs the fringe image phase distribution analysis method described in the above-mentioned example to calculate a relative phase difference between an object wave and a reference wave, thereby measuring the refractive index distribution of the object to be measured.

EXAMPLE 9

For an example of a program for executing the method according to the present invention, a program which executes the processes shown in FIGS. 4 to 6 in the example of the above-mentioned method using a personal computer is created by C and C++ languages and executed the method. Then, the execution result is displayed on a display device and then checked.

As described above, the program may be a general-purpose program which processes fringe image data using a general-purpose calculator and displays the result using a display device or a unique program suitable for various types of measurement devices and apparatuses described in Examples 5 to 8. In addition, the program may be a built-in type, an embedded type, a reading type, or a download type.

INDUSTRIAL APPLICABILITY

The present invention relates to a phase distribution measurement method and a device using the same and is particularly suitable to measure the shape and displacement of a three-dimensional object using the grating projection method, to evaluate the shape (for example, the thickness, flatness, and parallelism) of an optical component using an interferometer (for example, the Michelson interferometer, the Mach-Zehnder interferometer, and the Fizeau interferometer), or to measure the refractive index distribution of the optical component.

Specifically, examples of the industrial field to which the present invention can be applied include the manufacturing industry, the garment industry, the optical field, the civil engineering and construction field, and the medical field.

Examples of the device to which the present invention can be applied include three-dimensional shape deformation measurement devices, various types of optical interferometer devices, devices for measuring the thickness or refractive index distribution of a transparent material, imaging ultrasonic flaw detection devices, and phase-shift laser microscopes.

DESCRIPTION OF THE REFERENCE SYMBOLS

1: calculator
2: monitor
3: camera
4: grating projection device
5: object to be measured
6: laser
10: timing synchronization unit
11: phase-shift control unit
12: fringe grating image recording unit
13: phase analysis calculation unit
20: half mirror
21: reference mirror
22: PZT stage
23: plane mirror
24: grating pattern
25: objective lens
26: magnifying lens
27: biprism
41: thinning-out process and intensity interpolation process for every m pixels in x direction
42: thinning-out process and intensity interpolation process for every n pixels in y direction
43: two-dimensional discrete Fourier transform
44: addition of thinned-out phase distribution
51: phase shifting method
52: process for normalizing intensity of amplitude of fringe image
53: thinning-out process and intensity interpolation process for every m pixels in x direction
54: two-dimensional discrete Fourier transform
55: addition of thinned-out phase distribution
61: phase shifting method
62: process for normalizing intensity of amplitude of fringe image
63: thinning-out process and intensity interpolation process for every m pixels in x direction
64: thinning-out process and intensity interpolation process for every n pixels in y direction
65: three-dimensional discrete Fourier transform
66: addition of thinned-out phase distribution

The invention claimed is:

1. A method for analyzing a phase distribution of a fringe image that calculates a phase distribution of a fringe image obtained by capturing a fringe pattern on a surface of an object using an optical digital camera comprising an imaging element arranged in a horizontal direction and a vertical direction, the method comprising:
   a step of obtaining one two-dimensional fringe image or a three-dimensional fringe image in which a plurality of two-dimensional fringe images are arranged in time series by capturing one image of the fringe pattern on the surface of the object or a plurality of images of the fringe pattern while shifting a temporal phase;
   a step of generating a plurality of phase-shifted moiré fringe images by performing at least a thinning-out process on intensity data of the one two-dimensional fringe image or the three-dimensional fringe image;
   a step of calculating a phase distribution of the moiré fringe images in the horizontal direction or the vertical direction by using fast Fourier transform or discrete Fourier transform on the phase-shifted moiré fringe images by a calculator; and
   step of calculating the phase distribution of the fringe pattern image on the object by adding a phase value of a thinning-out point in the thinning-out process to a value of each point in the phase distribution by the calculator.

2. The method for analyzing a phase distribution of a fringe image according to claim 1, wherein:
   the step of obtaining the two-dimensional fringe image comprises capturing the fringe pattern that is arranged on the surface of the object so as to be inclined in one direction or two directions perpendicular to each other with respect to the arrangement of the imaging element of the optical digital camera in the horizontal and vertical directions; and
   the step of generating the plurality of phase-shifted moiré fringe images comprises,
   a sub-step of performing M thinning-out processes and N thinning-out processes (M and N are an integer equal to or greater than 3) on the two-dimensional fringe image while sequentially changing starting pixels in the horizontal direction and the vertical direction for every M pixels and every N pixels which are arranged at equal intervals in the horizontal direction and the vertical direction, respectively, and
   a sub-step of generating M×N-step moiré fringe images by performing an intensity value interpolation process on each of the images thinned out in the horizontal or vertical direction which are obtained by the thinning-out processes.

3. The method for analyzing a phase distribution of a fringe image according to claim 1, wherein:
   the step of obtaining the three-dimensional fringe image comprises obtaining a plurality of phase-shifted two-dimensional fringe images by capturing T-step images (T is an integer equal to or greater than 3) of the fringe pattern that is arranged on the surface of the object in the horizontal direction or the vertical direction or is arranged in a lattice shape in the horizontal direction and the vertical direction with respect to the arrangement of the imaging element of the optical digital camera in the horizontal and vertical directions, while shifting the temporal phase; and the step of generating the plurality of phase-shifted moiré fringe images comprises:

a pre-processing sub-step of converting the T-step two-dimensional fringe images whose temporal phases are shifted into T-step normalized two-dimensional fringe images with a constant intensity of amplitude, using an intensity of amplitude and an intensity distribution of a background calculated by a phase shifting method, when the intensity of amplitude distribution of the lattice-shaped fringe pattern is not constant;

a thinning-out sub-step of sampling every M pixels which are arranged at equal intervals in the horizontal direction or the vertical direction in each of the T-step two-dimensional fringe images with a constant intensity of amplitude whose temporal phases are shifted; and a sub-step of generating M×T-step moiré fringe images by performing an intensity value interpolation process on each of the M-step images which are thinned-out in the horizontal direction or the vertical direction by the thinning-out process.

4. The method for analyzing a phase distribution of a fringe image according to claim 1, wherein:

the step of obtaining the three-dimensional fringe image comprises obtaining a plurality of phase-shifted two-dimensional fringe images by capturing T-step images (T is an integer equal to or greater than 3) of the fringe pattern that is arranged on the surface of the object so as to be inclined in one direction or to be inclined in a lattice shape in two directions perpendicular to each other, with respect to the arrangement of the imaging element of the optical digital camera in the horizontal and vertical directions, while shifting the temporal phase; and the step of generating the plurality of phase-shifted moiré fringe images comprises:

a pre-processing sub-step of converting the T-step two-dimensional fringe images whose temporal phases are shifted into T-step normalized two-dimensional fringe images with a constant intensity of amplitude, using an intensity of amplitude and an intensity distribution of background calculated by a phase shifting method, only when the intensity of amplitude distribution of the fringe pattern is not constant;

a sub-step of performing M thinning-out processes and N thinning-out processes on each of the two-dimensional fringe images with the constant intensity of amplitude while sequentially changing starting pixels in the horizontal direction and the vertical direction for every M pixels and every N pixels which are arranged at equal intervals in the horizontal direction and the vertical direction, respectively; and a sub-step of generating M×N×T-step moiré fringe images for the T-step two-dimensional fringe images whose temporal phases are shifted by using the sub-step of performing the intensity value interpolation process on each of the images which are thinned out in the horizontal direction or the vertical direction by the thinning-out process to generate M×T-step moiré fringe images.

5. A measurement device which measures a three-dimensional shape, displacement, and distortion distribution of a structure and performs the method for analyzing a phase distribution of a fringe image according to claim 1.

6. A measurement device which measures a thickness, refractive index distribution, or inclination angle of an optical component and a transparent object and performs the method for analyzing a phase distribution of a fringe image according to claim 1.

7. A measurement device which detects a defect of an object using phase information of an ultrasonic image, detects anomalous displacement to detect a landslide, evaluates integrity of an infrastructure, and performs the method for analyzing a phase distribution of a fringe image according to claim 1.

8. A measurement device which non-invasively analyzes and evaluates a cell tissue of a living body and performs the method for analyzing a phase distribution of a fringe image according to claim 1.

9. A non-transitory processor-readable medium incorporating a program of instructions executable by an automated processor for analyzing a phase distribution of a fringe image by carrying out the steps according to claim 1.

* * * * *